(12) United States Patent
Scabellone et al.

(10) Patent No.: US 11,826,150 B2
(45) Date of Patent: Nov. 28, 2023

(54) USER INTERFACE FOR ANALYSIS OF ELECTROCARDIOGRAMS

(71) Applicant: KONINKLIJKE PHILIPS N.V., Eindhoven (NL)

(72) Inventors: Chiara Scabellone, Paris (FR); Cyril Gaudefroy, Paris (FR); Jia Li, Paris (FR); Benjamin Barre, Suresnes (FR)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/328,701

(22) PCT Filed: Aug. 24, 2018

(86) PCT No.: PCT/EP2018/072912
§ 371 (c)(1),
(2) Date: Feb. 26, 2019

(87) PCT Pub. No.: WO2019/038435
PCT Pub. Date: Feb. 28, 2019

(65) Prior Publication Data
US 2020/0022604 A1    Jan. 23, 2020

Related U.S. Application Data

(60) Provisional application No. 62/549,994, filed on Aug. 25, 2017.

(51) Int. Cl.
*A61B 5/352* (2021.01)
*G16H 50/20* (2018.01)
(Continued)

(52) U.S. Cl.
CPC .............. *A61B 5/352* (2021.01); *A61B 5/339* (2021.01); *G16H 40/63* (2018.01); *G16H 50/20* (2018.01)

(58) Field of Classification Search
CPC ...... A61B 5/0456; A61B 5/044; G16H 50/20; G16H 40/63
See application file for complete search history.

(56) References Cited

U.S. PATENT DOCUMENTS

| 5,024,225 A | 6/1991 | Fang |
|---|---|---|
| 5,239,494 A | 8/1993 | Golbeck |

(Continued)

FOREIGN PATENT DOCUMENTS

| CA | 2466848 A1 | 6/2003 |
|---|---|---|
| CN | 101268938 A | 9/2008 |

(Continued)

OTHER PUBLICATIONS

Alfonso et al., "ECG Beat Detection Using Filter Banks", Transactions on Biomedical Engineering, vol. 46, No. 2, Feb. 1999, pp. 192-202, Saint Paul, MN USA.

(Continued)

*Primary Examiner* — Mallika D Fairchild
*Assistant Examiner* — Shreya Anjaria

(57) ABSTRACT

The present invention relates to a computer-implemented method for electrocardiogram analysis, the method comprising the steps of receiving at least one ECG signal; analyzing the ECG signal to provide features and/or identify at least one episode and/or event, wherein an episode is a segment of the ECG signal defined by a starting time, a duration and a label obtained during the analysis of the ECG signal and an event is a strip of the ECG signal of predefined duration defined by a starting time and a label obtained during the analysis of the ECG signal; and displaying a multiple field display (1) which includes at least a main plot (42), being a global view of a graphic representation of the ECG signal in a first time window; a local view of a graphic representation of the ECG signal in a second time window (51), where the first time window comprises the second time window; an (Continued)

intermediate view of a graphic representation of the ECG signal in a third time window (52), wherein the third time window comprises the second time window and has a duration comprised between the duration of the first time window and the duration of the second time window.

24 Claims, 9 Drawing Sheets

(51) Int. Cl.
*G16H 40/63* (2018.01)
*A61B 5/339* (2021.01)

(56) References Cited

U.S. PATENT DOCUMENTS

| | | |
|---|---|---|
| 5,533,511 A | 7/1996 | Kaspari et al. |
| 5,619,991 A | 4/1997 | Sloane |
| 5,623,935 A | 4/1997 | Faisandier |
| 5,819,007 A | 10/1998 | Elghazzawi |
| 5,907,291 A | 5/1999 | Chen et al. |
| 5,966,692 A | 10/1999 | Langer et al. |
| 6,024,699 A | 2/2000 | Surwit et al. |
| 6,157,850 A | 12/2000 | Diab et al. |
| 6,424,860 B1 * | 7/2002 | Karlsson ............ A61B 5/7475 600/512 |
| 6,507,753 B1 | 1/2003 | Xue et al. |
| 6,612,985 B2 | 9/2003 | Eiffert et al. |
| 6,656,125 B2 | 12/2003 | Misczynski et al. |
| 6,694,177 B2 | 2/2004 | Eggers et al. |
| 7,142,907 B2 | 11/2006 | Xue et al. |
| 7,289,844 B2 | 10/2007 | Misczynski et al. |
| 7,941,207 B2 | 5/2011 | Korzinov |
| RE43,767 E | 10/2012 | Eggers et al. |
| 8,332,017 B2 | 12/2012 | Tarassenko et al. |
| 8,668,644 B2 | 3/2014 | Ong et al. |
| 8,684,900 B2 | 4/2014 | Tran |
| 8,818,496 B2 | 8/2014 | Dziubinski et al. |
| D717,955 S | 11/2014 | Bishay et al. |
| 8,903,479 B2 | 12/2014 | Zoicas |
| 8,932,220 B2 | 1/2015 | Ong et al. |
| 8,951,193 B2 | 2/2015 | Ong et al. |
| D744,659 S | 12/2015 | Bishay et al. |
| 9,241,650 B2 | 1/2016 | Amirim |
| 9,254,095 B2 | 2/2016 | Galloway et al. |
| 9,295,429 B2 | 3/2016 | Ong et al. |
| 9,339,202 B2 | 5/2016 | Brockway et al. |
| 9,345,414 B1 | 5/2016 | Bardy et al. |
| 9,351,652 B2 | 5/2016 | Dziubinski et al. |
| 9,364,155 B2 | 6/2016 | Bardy et al. |
| 9,408,545 B2 | 8/2016 | Felix et al. |
| 9,408,551 B2 | 8/2016 | Bardy et al. |
| 9,420,957 B2 | 8/2016 | Ong et al. |
| D766,447 S | 9/2016 | Bishay et al. |
| 9,433,367 B2 | 9/2016 | Felix et al. |
| 9,433,380 B1 | 9/2016 | Bishay et al. |
| 9,468,386 B2 | 10/2016 | Braojos Lopez et al. |
| 9,504,423 B1 | 11/2016 | Bardy et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,615,763 B2 | 4/2017 | Felix et al. |
| 9,619,660 B1 | 4/2017 | Felix et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,700,227 B2 | 7/2017 | Bishay et al. |
| D793,566 S | 8/2017 | Bishay et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,730,641 B2 | 8/2017 | Felix et al. |
| 9,737,211 B2 | 8/2017 | Bardy et al. |
| 9,737,224 B2 | 8/2017 | Bardy et al. |
| D801,528 S | 10/2017 | Bardy et al. |
| 9,775,536 B2 | 10/2017 | Felix et al. |
| 9,788,722 B2 | 10/2017 | Bardy et al. |
| 9,808,206 B1 | 11/2017 | Zhao et al. |
| 9,820,665 B2 | 11/2017 | Felix et al. |
| 9,901,274 B2 | 2/2018 | Bishay et al. |
| 9,936,875 B2 | 4/2018 | Bardy et al. |
| 9,955,885 B2 | 5/2018 | Felix et al. |
| 9,955,888 B2 | 5/2018 | Felix et al. |
| 9,955,911 B2 | 5/2018 | Bardy et al. |
| 10,004,415 B2 | 6/2018 | Bishay et al. |
| 10,045,709 B2 | 8/2018 | Bardy et al. |
| 10,052,022 B2 | 8/2018 | Bardy et al. |
| D831,833 S | 10/2018 | Bishay et al. |
| 10,111,601 B2 | 10/2018 | Bishay et al. |
| 10,123,703 B2 | 11/2018 | Bardy et al. |
| 10,154,793 B2 | 12/2018 | Felix et al. |
| D838,370 S | 1/2019 | Bardy et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,426,364 B2 | 10/2019 | Rapin et al. |
| 10,492,730 B1 | 12/2019 | Mehta |
| 10,568,570 B1 | 2/2020 | Sherpa |
| 10,758,139 B2 | 9/2020 | Rapin et al. |
| 10,779,744 B2 | 9/2020 | Rapin et al. |
| 10,827,938 B2 | 11/2020 | Fontanarava et al. |
| 10,959,660 B2 | 3/2021 | Li et al. |
| 11,134,880 B2 | 10/2021 | Rapin et al. |
| 11,147,500 B2 | 10/2021 | Li et al. |
| 11,331,034 B2 | 5/2022 | Rapin et al. |
| 2001/0029338 A1 | 10/2001 | Krishnamachari |
| 2002/0169487 A1 | 11/2002 | Graindorge |
| 2003/0176795 A1 | 9/2003 | Harris et al. |
| 2004/0147840 A1 | 7/2004 | Duggirala et al. |
| 2004/0230105 A1 | 11/2004 | Geva et al. |
| 2004/0260192 A1 * | 12/2004 | Yamamoto ............ A61B 5/044 600/523 |
| 2005/0101873 A1 | 5/2005 | Misczynski et al. |
| 2005/0113706 A1 | 5/2005 | Prystowsky |
| 2005/0171448 A1 | 8/2005 | Korzinov |
| 2005/0182334 A1 | 8/2005 | Korzinov |
| 2005/0222508 A1 | 10/2005 | Moreno et al. |
| 2006/0020219 A1 | 1/2006 | Zinser, Jr. et al. |
| 2006/0173369 A1 | 8/2006 | Kaski |
| 2007/0129642 A1 | 6/2007 | Korzinov |
| 2007/0191723 A1 | 8/2007 | Prystowsky et al. |
| 2007/0227606 A1 | 10/2007 | Sakazaki |
| 2007/0244402 A1 | 10/2007 | Brockway et al. |
| 2008/0004904 A1 | 1/2008 | Tran |
| 2008/0082016 A1 | 4/2008 | Kohls et al. |
| 2008/0103403 A1 | 5/2008 | Cohen |
| 2008/0132799 A1 | 6/2008 | Xue |
| 2008/0167567 A1 | 7/2008 | Bashour et al. |
| 2009/0112110 A1 | 4/2009 | Zhang |
| 2009/0192394 A1 | 7/2009 | Guttag et al. |
| 2010/0030302 A1 * | 2/2010 | Blowers ................ G16H 40/67 705/2 |
| 2010/0056940 A1 | 3/2010 | Moorman et al. |
| 2010/0076331 A1 | 3/2010 | Chan et al. |
| 2010/0217144 A1 | 8/2010 | Brian |
| 2010/0268103 A1 | 10/2010 | McNamara |
| 2011/0184297 A1 | 7/2011 | Vitali et al. |
| 2011/0224565 A1 | 9/2011 | Ong et al. |
| 2011/0257548 A1 | 10/2011 | Dong et al. |
| 2011/0282225 A1 * | 11/2011 | Anderson ............ A61B 5/0006 600/510 |
| 2011/0301435 A1 | 12/2011 | Albert et al. |
| 2012/0101398 A1 * | 4/2012 | Ramanathan .......... A61B 5/339 600/523 |
| 2012/0110226 A1 | 5/2012 | Vlach |
| 2012/0203491 A1 | 8/2012 | Sun et al. |

(56) References Cited

U.S. PATENT DOCUMENTS

| | | | |
|---|---|---|---|
| 2012/0278099 A1* | 11/2012 | Kelly | G16H 10/60 705/2 |
| 2013/0116585 A1 | 5/2013 | Bouguerra | |
| 2013/0184599 A1 | 7/2013 | Friedman et al. | |
| 2013/0237776 A1 | 9/2013 | Ong et al. | |
| 2014/0005988 A1 | 1/2014 | Brockway | |
| 2014/0073486 A1 | 3/2014 | Ahmed et al. | |
| 2014/0107493 A1 | 4/2014 | Yuen et al. | |
| 2014/0128758 A1 | 5/2014 | Galloway et al. | |
| 2014/0148714 A1 | 5/2014 | Mamaghanian et al. | |
| 2014/0187988 A1 | 7/2014 | Ong et al. | |
| 2014/0188770 A1 | 7/2014 | Agrafioti et al. | |
| 2014/0228665 A1 | 8/2014 | Albert | |
| 2014/0275840 A1 | 9/2014 | Osorio | |
| 2014/0330147 A1 | 11/2014 | Ousdigian et al. | |
| 2015/0008802 A1 | 1/2015 | Fukuda | |
| 2015/0018702 A1 | 1/2015 | Galloway et al. | |
| 2015/0051505 A1 | 2/2015 | Rossi | |
| 2015/0088020 A1 | 3/2015 | Dreisbach et al. | |
| 2015/0088024 A1 | 3/2015 | Sackellares et al. | |
| 2015/0105640 A1 | 4/2015 | Friedman et al. | |
| 2015/0119725 A1 | 4/2015 | Martin et al. | |
| 2015/0164349 A1 | 6/2015 | Gopalakrishnan et al. | |
| 2015/0190067 A1 | 7/2015 | Prystowsky | |
| 2015/0223759 A1 | 8/2015 | Ong et al. | |
| 2015/0238151 A1 | 8/2015 | Sitzman et al. | |
| 2015/0248534 A1* | 9/2015 | Krzywicki | G06F 3/04842 715/771 |
| 2015/0257668 A1 | 9/2015 | Braojos Lopez et al. | |
| 2015/0282726 A1 | 10/2015 | Grube et al. | |
| 2015/0289112 A1 | 10/2015 | Gilbert et al. | |
| 2016/0051157 A1 | 2/2016 | Waydo | |
| 2016/0058318 A1 | 3/2016 | Borjigin et al. | |
| 2016/0085927 A1 | 3/2016 | Dettinger et al. | |
| 2016/0085937 A1 | 3/2016 | Dettinger et al. | |
| 2016/0086297 A1 | 3/2016 | Dettinger et al. | |
| 2016/0098536 A1 | 4/2016 | Dettinger et al. | |
| 2016/0098537 A1 | 4/2016 | Dettinger et al. | |
| 2016/0098538 A1 | 4/2016 | Dettinger et al. | |
| 2016/0135706 A1 | 5/2016 | Sullivan et al. | |
| 2016/0150989 A1 | 6/2016 | Felix et al. | |
| 2016/0183827 A1 | 6/2016 | Xue et al. | |
| 2016/0183829 A1 | 6/2016 | Friedman et al. | |
| 2016/0192850 A1 | 7/2016 | Gregg et al. | |
| 2016/0192853 A1 | 7/2016 | Bardy et al. | |
| 2016/0235319 A1 | 8/2016 | Albert | |
| 2016/0242665 A1 | 8/2016 | Galloway et al. | |
| 2016/0249823 A1 | 9/2016 | Galloway et al. | |
| 2016/0262646 A1 | 9/2016 | Bardy et al. | |
| 2016/0321430 A1 | 11/2016 | Eckman et al. | |
| 2016/0345854 A1 | 12/2016 | Bardy et al. | |
| 2016/0345909 A1 | 12/2016 | Felix et al. | |
| 2016/0367187 A1 | 12/2016 | Ahmed et al. | |
| 2017/0014037 A1 | 1/2017 | Coppola et al. | |
| 2017/0095153 A1 | 4/2017 | Bardy et al. | |
| 2017/0098047 A1 | 4/2017 | Young | |
| 2017/0105683 A1 | 4/2017 | Xue | |
| 2017/0112401 A1 | 4/2017 | Rapin et al. | |
| 2017/0135579 A1 | 5/2017 | Bardy et al. | |
| 2017/0177811 A1 | 6/2017 | Mcfarland et al. | |
| 2017/0188872 A1 | 7/2017 | Hughes et al. | |
| 2017/0238833 A1 | 8/2017 | Felix et al. | |
| 2017/0251948 A1 | 9/2017 | Felix et al. | |
| 2017/0258358 A1 | 9/2017 | Bishay et al. | |
| 2017/0340206 A1 | 11/2017 | Bardy et al. | |
| 2017/0340290 A1 | 11/2017 | Felix et al. | |
| 2017/0357764 A1* | 12/2017 | Fauss | A61B 5/7435 |
| 2017/0367609 A1 | 12/2017 | Bardy et al. | |
| 2018/0020939 A1 | 1/2018 | Albert | |
| 2018/0028144 A1 | 2/2018 | Chen et al. | |
| 2018/0060522 A1 | 3/2018 | Petterson et al. | |
| 2018/0146875 A1 | 5/2018 | Friedman et al. | |
| 2018/0177423 A1 | 6/2018 | Bishay et al. | |
| 2018/0206752 A1 | 7/2018 | Bardy et al. | |
| 2018/0242876 A1 | 8/2018 | Hughes et al. | |
| 2018/0279956 A1 | 10/2018 | Waydo et al. |
| 2018/0289274 A1 | 10/2018 | Bahney et al. |
| 2018/0296118 A1 | 10/2018 | Bishay et al. |
| 2018/0310892 A1 | 11/2018 | Perschbacher et al. |
| 2018/0344189 A1 | 12/2018 | Dusan |
| 2018/0344191 A1 | 12/2018 | Bardy et al. |
| 2018/0353071 A1 | 12/2018 | Bardy et al. |
| 2018/0368715 A1 | 12/2018 | Xue et al. |
| 2018/0374576 A1 | 12/2018 | Dettinger et al. |
| 2019/0034050 A1 | 1/2019 | Williams et al. |
| 2019/0038149 A1 | 2/2019 | Gopalakrishnan et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104951 A1 | 4/2019 | Valys et al. |
| 2019/0104961 A1 | 4/2019 | Felix et al. |
| 2019/0117068 A1 | 4/2019 | Thomson et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |
| 2019/0133483 A1 | 5/2019 | Xue et al. |
| 2019/0133486 A1 | 5/2019 | Felix et al. |
| 2019/0167141 A1 | 6/2019 | Duckert et al. |
| 2019/0167143 A1 | 6/2019 | Li et al. |
| 2019/0223739 A1 | 7/2019 | Rapin et al. |
| 2019/0259496 A1 | 8/2019 | Pemberton et al. |
| 2019/0267139 A1 | 8/2019 | Hutchins et al. |
| 2019/0272920 A1 | 9/2019 | Teplitzky |
| 2019/0274563 A1 | 9/2019 | Soli et al. |
| 2019/0274574 A1 | 9/2019 | Hughes et al. |
| 2019/0282118 A1 | 9/2019 | Kaski |
| 2019/0298204 A1 | 10/2019 | Fontanarava et al. |
| 2019/0357794 A1 | 11/2019 | Bardy et al. |
| 2020/0013507 A1 | 1/2020 | Braun et al. |
| 2020/0015694 A1 | 1/2020 | Rapin et al. |
| 2020/0022591 A1 | 1/2020 | Drakulic et al. |
| 2020/0029911 A1 | 1/2020 | Chakravarthy et al. |
| 2020/0060563 A1 | 2/2020 | Boleyn et al. |
| 2020/0118673 A1 | 4/2020 | Dettinger et al. |
| 2020/0155025 A1 | 5/2020 | Smith et al. |
| 2020/0178825 A1 | 6/2020 | Lu et al. |
| 2020/0205745 A1 | 7/2020 | Khosousi et al. |
| 2020/0237317 A1 | 7/2020 | Newberry et al. |
| 2020/0242763 A1 | 7/2020 | Bhuiyan et al. |
| 2020/0273567 A1 | 8/2020 | Petterson et al. |
| 2020/0289014 A1 | 9/2020 | Park et al. |
| 2020/0289033 A1 | 9/2020 | Sivertsen et al. |
| 2020/0289063 A1 | 9/2020 | Mehta |
| 2020/0297286 A1 | 9/2020 | Costa et al. |
| 2020/0397313 A1 | 12/2020 | Attia et al. |
| 2020/0401684 A1 | 12/2020 | Vath et al. |
| 2021/0000344 A1 | 1/2021 | Dreisbach et al. |
| 2021/0000365 A1 | 1/2021 | Rapin et al. |
| 2021/0076960 A1 | 3/2021 | Fornwalt et al. |
| 2021/0150693 A1 | 5/2021 | Fornwalt et al. |
| 2021/0204859 A1 | 7/2021 | Moll |
| 2021/0271847 A1 | 9/2021 | Courtiol et al. |

FOREIGN PATENT DOCUMENTS

| | | |
|---|---|---|
| CN | 101766484 A | 7/2010 |
| CN | 102188240 A | 9/2011 |
| CN | 102379694 A | 3/2012 |
| CN | 102779234 A | 11/2012 |
| CN | 103038772 A | 4/2013 |
| CN | 103110417 A | 5/2013 |
| CN | 103284702 A | 9/2013 |
| CN | 103417209 A | 12/2013 |
| CN | 104463326 A | 3/2015 |
| CN | 104970789 A | 10/2015 |
| CN | 106778685 A | 5/2017 |
| DE | 60127354 T2 | 12/2007 |
| EP | 0465241 A2 | 1/1992 |
| EP | 0 465 241 B1 | 11/1998 |
| EP | 1 179 319 A1 | 2/2002 |

(56) References Cited

FOREIGN PATENT DOCUMENTS

| | | |
|---|---|---|
| EP | 1 503 664 A2 | 2/2005 |
| EP | 2 030 565 A1 | 3/2009 |
| EP | 2534597 A2 | 12/2012 |
| EP | 3 144 851 A1 | 3/2017 |
| EP | 2 534 597 B1 | 10/2018 |
| JP | 2002172096 A | 6/2002 |
| JP | 2010233953 A | 10/2010 |
| JP | 2013524865 A | 6/2013 |
| JP | 2016202347 A | 12/2016 |
| KR | 20150020955 A | 2/2015 |
| WO | WO-9738626 A1 | 10/1997 |
| WO | WO-03/045224 A2 | 6/2003 |
| WO | WO-03045224 A3 | 11/2004 |
| WO | WO-2006/048881 A2 | 5/2006 |
| WO | WO-2011/115576 A2 | 9/2011 |
| WO | WO-2012140559 A1 | 10/2012 |
| WO | WO-2016110804 A1 | 7/2016 |
| WO | WO-2016/145392 A1 | 9/2016 |
| WO | WO-2016145392 A1 * 9/2016 ......... A61B 5/02405 |
| WO | WO-2017/072250 A1 | 5/2017 |
| WO | WO-2019/038435 A1 | 2/2019 |
| WO | WO-2019089830 A1 | 5/2019 |
| WO | WO-2019147180 A1 | 8/2019 |
| WO | WO-2020086865 A1 | 4/2020 |
| WO | WO-2020161605 A1 | 8/2020 |

OTHER PUBLICATIONS

Almeida et al., "Multilead ECG Delineation Using Spatially Projected Leads From Wavelet Transform Loops", IEEE Transactions on biomedical engineering, vol. 56, No. 8, Aug. 2009, pp. 1996-2005, Zaragoza, Spain.
Badilini et al., ECGScan: A Method for Conversion of Paper Electrocardiographic Printouts to Digital Electrocardiographic Files, Journal of Electrocardiology, 38:310-318 (2005).
Bishop, "Pattern Recognition and Machine Learning", Springer, Information Science and Statistics, 2006, ISBN-10: D-387-31073-8, New York, NY, USA.
Boichat et al., "Wavelet-Based ECG Delineation on a Wearable Embedded Sensor Platform", Proceedings of Wearable and Implantable Body Sensor Networks, 2009, pp. 256-261, Madrid, Spain.
Dr. Dobbs Journal, "Neural Nets and Noise Filtering", p. 32, Jan. 1, 1989.
Chazal et al., "A Patient-Adapting Heartbeat Classifier Using ECG Morphology and Heartbeat Interval Features", EEE Transactions on Biomedical Engineering, Dec. 2006, vol. 53, No. 12, pp. 2535-2543, Dublin, Ireland.
Chazal et al., "Automatic classification of heartbeats using ECG morphology and heartbeat interval features", IEEE Transactions on Biomedical Engineering, Jul. 2004, vol. 51, No. 7, pp. 1196-1206, Dublin, Ireland.
Chebil, et al., A Novel Method for Digitizing Standard ECG Papers, Proceedings of the International Conference on Computer and Communication Engineering 2008, pp. 1308-1312, May 13-15, 2008, Kuala Lumpur, Malaysia.
Choi et al., "Development of ECG beat segmentation method by combining lowpass filter and irregular R-R interval pheckup strategy", Expert Systems with Applications, vol. 37 (2010) pp. 5208-5218, Seoul, Republic of Korea.
Coast et al., "An Approach to Cardiac Arrhythmia Analysis Using Hidden Markov Models", IEEE transactions on biomedical engineering, vol. 37, No. 9, Sep. 1990, pp. 826-836, Pittsburgh, PA, US.
Cybenko, "Approximation by Superpositions of a Sigmoidal Function", Mathematics of Control, Signals and Systems, vol. 2, 1989, pp. 303-314, Urbana, Illinois, USA.
Donahue et al., "Long-term Recurrent Convolutional Networks for Visual Recognition and Description", arXiv:1411.4389v3, pp. 1-13, Feb. 17, 2015, Berkeley, CA, USA.
Dubois et al., "Automatic ECG wave extraction in long-term recordings using Gaussian mesa function models and nonlinear probability estimators", Computer Methods and Programs in Biomedicine, Mar. 2007, vol. 88, pp. 217-233, Pads, France.
EP Search Report and Written Opinion dated Oct. 15, 2018 in EP Patent Appl. Serial No. 18305376.8.
EP Search Report dated Apr. 13, 2016 in European Patent Appl. Serial No. 15191769.7.
Francois Portet, "P wave detector with PP rhythm tracking: Evaluation in different arrhythmia contexts", Physiological Measurement, Institute of Physics: Hybrid Open Access, 2008, 29, pp. 141-155, Scotland, UK.
Fukushima, "Neocognitron: A Self-organizing Neural Network Model for a Mechanism of Pattern Recognition Unaffected by Shift in Position", Biological Cybernetics, vol. 36, 1980, pp. 193-202, Tokyo, Japan.
Hughes et al., "Markov Models for Automated ECG Interval Analysis", Proceedings of Neural Information Processing Systems, 2004, pp. 611-618, Oxford, UK.
Ieva et al., "Multivariate functional clustering for the morphological analysis of electrocardiogram curves", Journal of The Royal Statistical Society: Series C (Applied Statistics), Blackwell Publishing Ltd, London, UK, 2013, vol. 62, pp. 401-418.
International Search Report & Written Opinion dated Jan. 24, 2017 in Int'l PCT Patent Appl. Serial No. PCT/EP2016/075972.
International Search Report & Written Opinion dated Nov. 21, 2018 in Int'l PCT Patent Appl. Serial No. PCT/EP2018/072912.
Jin et al., "Deep learning research on clinical electrocardiogram analysis", Science China Press, vol. 45, No. 3, 2015, pp. 398-416, China, English abstract provided.
Johson et al., "R-Peak Estimation using Multimodal Lead Switching", Computing in Cardiology 2014, pp. 281-284, Oxford, UK.
Kaur et al., "Comparison of different approaches for removal of Baseline wander from ECG signal", Proceedings published by International Journal of Computer Applications, 2011, pp. 30-36, Sangrur (Pb.), India.
Kiranyaz et al, "Real-Time Patient-Specific ECG Classification by 1-D Convolutional Neural Networks", IEEE Transactions on Biomedical Engineering , 63(3):664-675 (2016).
Kiranyaz et al., "Convolutional Neural Networks for Patient-Specific ECG Classification", 37th Annual International Conference of the IEEE Engineering in Medicine and Biology Society (EMBC). Proceedings IEEE Piscataway, N.J., US, Aug. 2015, pp. 2608-2611.
Krizhevsky et al., "ImageNet Classification with Deep Convolutional Neural Networks", Proceedings of Neural Information Processing Systems, 2012, pp. 1097-1105, Toronto, Canada.
Laguna et al., "A Database for Evaluation of Algorithms for Measurement of QT and Other Waveform Intervals in the ECG", Computers in Cardiology, 1997, vol. 24, pp. 673-676, Spain.
LeCun et al., "Backpropagation Applied to Handwritten Zip Code Recognition", Neural Computation, vol. 1, 1989, pp. 541-551, Holmdel, NJ, USA.
Li et al., "Detection of ECG Characteristic Points Using Wavelet Transforms", Transactions on Biomedical Engineering, vol. 42, No. 1, Jan. 1995, pp. 21-28, Shaanxi, P. R. China.
Li et al., Deep Neural Networks Improve Atrial Fibrillation Detection in Detection in Holter: First Results, Eurupean Journal of Preventive Cardiology, European Congress on eCardiology & eHealth, Oct. 2016, Abstract, 23 (2S), 41 (2016).
Lin et al., "Beat-to-beat P and T wave delineation in ECG signals using a marginalized particle filter", Proceedings of EUSIPCO, 2012, Toulouse, France, pp. 479-483.
Lin et al., "P and Twave Delineation Andwaveform Estimation in ECG Signals Using a Block Gibbs Sampler", Signal Processing Conference (EUSIPCO), 2012, pp. 479-483, Toulouse, France.
Lin et al., "P- and T-Wave Delineation in ECG Signals Using a Bayesian Approach and a Partially Collapsed Gibbs Sampler", IEEE Transactions on Biomedical Engineering Dec. 2010, Toulouse France vol. 57 pp. 2840-2849.
Long et al., "Fully Convolutional Networks for Semantic Segmentation", Proceedings of Computer Vision and Pattern Recognition, 2015, pp. 3431-3440, Berkeley, CA, USA.
Martinez et al., "A Wavelet-Based ECG Delineator: Evaluation on Standard Databases" IEEE transactions on biomedical engineering, vol. 51, No. 4, Apr. 2004, 570-581, Zaragoza, Spain.

(56) References Cited

OTHER PUBLICATIONS

Matan et al., "Multi-Digit Recognition Using A Space Displacement Neural Network", Neural Information Processing Systems, Morgan Kaufmann, 1992, pp. 488-495, Holmdel, NJ USA.
Megriche, et al., On the Analysis of a Compound Neural Network for Detecting Atrio Ventricular Heart Block (AVB) in a ECG Signal, International Journal of Medical, Health, Biomedical, Bioengineering and Pharmaceutical Engineering, 2(3):68-78 (2008).
Megriche, et al., On the Analysis of a Compound Neural Network for Detecting Atrio Ventricular Heart Block (AVB) in an ECG Signal, International Journal of Biological and Life Sciences, 4(1):1-11 (2008).
Mnih et al., "Recurrent Models of Visual Attention", Google DeepMind, arXiv:1406.6247v1, pp. 1-12, Jun. 24, 2014.
Noda et al., "Audio-visual speech recognition using deep learning", Appl Intell 2015, vol. 42, pp. 722-737, Springer Science, published Dec. 20, 2014, New York, NY USA.
Nowlan et al., "A Convolutional Neural Network Hand Tracker", Advances in Neural Information Processing Systems 7, Morgan Kaufmann, 1995, pp. 901-908, Synaptics, Inc. San Jose, CA USA.
Pan et al., "A Real-Time QRS Detection Algorithm", IEEE Transactions on Biomedical Engineering, vol. BME-32, No. 3, Mar. 1985, pp. 230-236, Shanghai, P.R. of China.
Pigoli et al., "Wavelets in functional data analysis: Estimation of multidimensional curves and their derivatives", Computational Statistics and Data Analysis, vol. 56, 2012, pp. 1482-1498, Politecnico di Milano, Italy.
Prineas et al., "The Minnesota Code Manual of Electrocardiographic Findings", Springer, Second Edition, ISBN D78-1-84882-777-6, 2009, Minneapolis, Minnesota, US.
Ravichandran, et al., Novel Tool for Complete Digitization of Paper Electrocardiography Data, IEEE Journal of Translational Engineering in Health and Medicine, Medical Imaging and Diagnostic Radiology, vol. 1, 7 pages, Jun. 2013.
Rodrigues et al.,. "A Neural Network Approach to ECG Denoising", CoRR, Dec. 2012, abs/1212.5217, pp. 1-15, Caparica, Portugal.
Rosenblatt, "The Perceptron: A Probabilistic Model for Information Storage and Organization in the Brain", Psychological Review, vol. 65, No. 6, 1958, pp. 386-408, Buffalo, NY, USA.
Russakovsky et al., "ImageNet Large Scale Visual Recognition Challenge", arXiv:1409.0575v3, pp. 1-43, Jan. 30, 2015, Stanford, CA, USA.
Saini et al., "Automated ECG Delineation using Machine Learning Algorithms", International Congress on Electrocardiology, 2014, pp. 1-4, Jalandhar, India.
Schluter et al., "Improved Musical Onset Detection With Convolutional Neural Networks", EEE International Conference on Acoustics, Speech, and Signal Processing ICASSP 2014,99 1-5, Linz, Austria.
Shen et al., "Multi-level ECG Classification Based on Independent Component Analysis and Support Vector Machine," Biomedical Engineering and Informatics (BMEI), 2010, vol. 3, pp. 960-964.
Simonyan et al., Very Deep Convolutional Networks for Large-Scale Image Recognition, Published as a conference paper at ICLR, Apr. 10, 2015.
Smith et al., Improved Interpretation of Atrial Dyshrthmias by a New Neural Network Electrocardiogram Interpretation Algorithm, Society for Academic Emergency Medicine Abstracts, 24 (S1), S235 (2017).
Statement of Validation and Accuracy for the Glasgow 12-Lead ECG Analysis Program, Physio Control, Mar. 2009, Redmond, WA USA.
Vaessen, "An approach to ECG Delineation using Wavelet Analysis and Hidden Markov Models", Universiteit Maastricht Institute of Instrument Development Engineering & Evaluation Master Thesis, Sep. 2006.

Zeiler, Matthew D., Adadelta: An Adaptive Learning Rate Method-,dated Dec. 22, 2012, prepared while at Google Inc., USA. (arXiv: 1212.5701 [cs.LG].
Zhang et al., "Improving object detection with deep convolutional networks via bayesian optimization and structured prediction", Computer Vision Foundation CVPR2015, pp. 249-258, Zhejiang, China.
Zheng et al., "Time Series Classification Using Multi-Channels Deep Convolutional Neural Networks", Web-Age nformation Management, 2014, vol. 8485, pp. 298-310, Switzerland.
International Search Report & Written Opinion dated Aug. 1, 2019 in Int'l PCT Patent Appl. Serial No. PCT/IB2019/052517.
International Search Report & Written Opinion dated Jun. 4, 2020 in Int'l PCT Patent Appl. Serial No. PCT/IB2020/050850.
Attia, et al., An artificial intelligence-enabled ECG algorithm for the identification of patients with atrial fibrillation during sinus rhythm: a retrospective analysis of outcome prediction, The Lancet, 394(10201):861-867 (Sep. 2019).
Christopoulos, et al., Artificial Intelligence—Electrocardiography to Predict Incident Atrial Fibrillation—A Population-Based Study, Circulation: Arrhythmia and Electrophysiology, 13(12):e009355 (Dec. 2020).
Extended EP Search Report dated Apr. 12, 2021 in EP Patent Application Serial No. 20211449.2.
Extended European Search Report dated Jul. 20, 2021 in EP Patent Appl. Serial No. 21167613.5.
Fiorina, AI-Based Strategy Enables Faster Holter ECG Analysis With Equivalent Clinical Accuracy Compared to a Classical Strategy, EP Europace, vol. 22, Issue Supplement 1, Abstract 222 (Jun. 2020).
Fiorina, et al., Artificial Intelligence Based Platform Enables Faster Ambulatory Electrocardiogram Analysis With Equivalent Clinical Accuracy Compared to Traditional Solution, Circulation, vol. 140, Issue Suppl. 1, Abstract 9825 (Nov. 2019).
International Search Report & Written Opinion dated Jan. 14, 2022 in Int'l PCT Patent Appl. Serial No. PCT/IB2021/0058958.
International Search Report & Written Opinion dated Jan. 31, 2022 in Int'l PCT Patent Appl. Serial No. PCT/IB2021/057341.
Maille, et al., Smartwatch Electrocardiogram and Artificial Intelligence for Assessing Cardiac-Rhythm Safety of Drug Therapy in the COVID-19 Pandemic. The QT-logs study, International Journal of Cardiology, 331:333-339 (May 2021).
Mittal, et al., AI Filter Improves Positive Predictive Value of Atrial Fibrillation Detection by an Implantable Loop Recorder, JACC: Clinical Electrophysiology, available online Feb. 10, 2021, https://doi.org/10.1016/j.jacep.2020.12.006.
Mittal, et al., An Artificial Intelligence-based Solution To Reduce False Positive Detections of Atrial Fibrillation By An Implantable Loop Recorder, available at https://cslide-us.ctimeetingtech.com/hrs20/attendee/eposter/file/195#1 (retrieved Jul. 23, 2021).
Raghunath, et al., Deep Neural Networks Can Predict New-Onset Atrial Fibrillation From the 12-Lead ECG and Help Identify Those At Risk of Atrial Fibrillation-Related Stroke, Circulation, 143(13):1287-98 (Mar. 2021).
Smith, et al., A deep neural network for 12-lead electrocardiogram interpretation outperforms a conventional algorithm, and its physician overread, in the diagnosis of atrial fibrillation, IJC Heart & Vasculature, 25:100423 (Dec. 2019).
Smith, et al., A deep neural network learning algorithm outperforms a conventional algorithm for emergency department electrocardiogram interpretation, Journal of Electrocardiology, 52:88-95 (Jan. 2019).
Smith, et al., Improved Interpretation of Atrial Dysrhythmias by a New Neural Network Electrocardiogram Interpretation Algorithm, Academic Emergency Medicine, vol. 24, S1, Abstract 670 (May 2017).
Artis, et al., Detection of Atrial Fibrillation Using Artificial Neural Networks, Proceedings Computers in Cardiology, pp. 173-176 (1991).

* cited by examiner

Cardiologs 15 rue de l'École de Médecine, 75006 Paris France

Sample Report

Max HR
Day 1 / 11:09:31                                                                 HR 68 bpm

Min HR
Day 1 / 11:20:24                                                                 HR 37 bpm

AV block
Day 1 / 11:00:00                                                    Type 2nd degree, Mobitz II Day 1 / 11:01:30                                                    Type 2nd degree, Mobitz II

USER INTERFACE FOR ANALYSIS OF ELECTROCARDIOGRAMS

CROSS-REFERENCE TO RELATED APPLICATIONS

This application is a national phase of international PCT Patent Application Serial No. PCT/EP2018/072912, filed Aug. 24, 2018, which claims priority to U.S. Provisional Patent Application Ser. No. 62/549,994, filed Aug. 25, 2017, the entire contents of each which are incorporated herein by reference.

FIELD OF INVENTION

The present invention pertains to the field of cardiology. In particular, the invention relates to the analysis of electrocardiographic data using a graphical user interface.

BACKGROUND OF INVENTION

Cardiac Holter monitoring devices (often simply Holter) are portable electrocardiographic devices for cardiac monitoring (the monitoring of the electrical activity of the cardiovascular system) for long time lapses (ranging from several minutes to several weeks). The data recorded by these devices is analyzed by professionals for the diagnosis of heart activity abnormalities, including arrhythmias such as atrial fibrillation. Guaranteeing an exact diagnosis requires an extensive analysis of the large amount of data available. The aim of an interface for long duration electrocardiographic (ECG) recordings is to improve the efficiency of the analysis and diminish the time consumption of such a task. The amount of data collected by an Holter device in a standard ambulatory use is large and the classical analysis performed by the clinician, who has to visually analyze the whole duration of the electrocardiographic (ECG) recordings, is inefficient and time consuming.

Recently, several platforms have become available to clinicians to facilitate this otherwise time consuming task. Said platforms allow an easier visualization of the ECG signal and sometimes the detection and visualization on the ECG signal of some clinically relevant ECG patterns. The platform may further allow the clinicians to navigate through the ECG signal and represent multiple plots at the same time.

However, to allow the physicians to significantly reduce the working time and improve the quality of the ECG analysis and of the report produced thereof, there is a need of developing a platform with upgraded interactivity solutions. To further improve the efficiency of an interactive platform, it is also needed to offer plots that encapsulate both more comprehensively and more synthetically the characteristics of the signal.

Furthermore, these types of platforms generally require a high computation power which is unpractical and the results of the analysis are only available locally on the platform which produced the analysis.

Definitions

In the present invention, the following terms have the following meanings:
  "ECG" refers to the process of recording the electrical activity of the heart over a period of time using electrodes placed on the skin.
  "ECG signal": refers to signals resulting from the recording of the electrical conduction in the heart. Said cardiac signal may be for instance an electrocardiogram (ECG). Such signals may have one or more channels, called leads. It may be short term (10 seconds in standard ECGs) or long term (several days in Holters).
  "Main plot": refers to a plot representing a simplified view of the whole signal corresponding to any kind of measure that can be calculated from the ECG signal (R-R plot, mean heart-rate plot, etc.) through time (x-axis is time).
  "R-R interval": refers to the interval between two QRS waves (more simply called R waves), where the QRS wave is considered the most prominent part of a heart beat.
  "R-R plot": refers to a plot of R-R intervals of an ECG signal through time, wherein an R-R interval is the time interval between two consecutive heart beats.
  "Cursor": refers to an element of display, used to select a particular timepoint of the signal.
  "Label": refers to any specification of the signal, should it be a cardiac abnormality (atrial fibrillation, ventricular premature complex, etc.), a cardiac description (normal sinus rhythm) or a description of the signal in itself (presence of noise), or a patient event (button pressed during exam for instance).
  "Episode": refers to a segment of the ECG signal comprised in a period of time associated to a label. An episode is characterized by an onset timepoint representing the beginning of the episode, an offset timepoint representing the end of the episode and a label. A same label can appear in several episodes on an ECG signal.
  "Strip": refers to a displayed extract of the signal of predefined fixed duration and is defined by a time point associated to the beginning of the strip. The strip can show one or several leads of the signal at once.
  "Burden": refers to the ratio of the duration of a given abnormality to the whole signal duration or number of occurrences of a given abnormality in the ECG signal.
  "Report": refers to a document or web page which summarizes information that a user wants to keep as a record about the holter. This typically includes abnormality burdens and a selection of strips.
  "Holter": refers to a type of ambulatory electrocardiography device, a portable device for cardiac monitoring (the monitoring of the electrical activity of the cardiovascular system) during at least 24 hours (often for two weeks at a time).
  "Multiple field display": refers to an ensemble comprising at least two distinct plots.
  "Event": refers to a time point corresponding to a characteristic variation on the ECG signal such as the onset of a waveform.
  "Classification" refers to the task of categorizing objects into a list of groups. Such a task includes for instance recognizing an animal from a picture (the list of groups is then a list of animals) or recognizing whether an ECG is normal or abnormal. It can be a multi-label classification, so that one object can be part of one or several groups of a given list of groups. An example of multi-label classification in the case of ECGs is classifying a portion of ECG signal as normal or as one of several possible abnormalities.
  "Delineation" refers to the identification of the temporal localization of each of the waves of a cardiac signal.

Delineation can also optionally provide more precise characterization of each of the waves.

"Real time" refers to a process for which the output is given within a time delay that is considered smaller than the time delay required to perform the underlying task of modulation adequately. Therefore, for self-paced modulation, real time refers to a process implemented in less than 700 ms, preferably less than 500 ms, more preferably less than 400 ms, even more preferably less than 250 ms.

SUMMARY

The present invention relates to a computer-implemented method for electrocardiogram analysis, the method comprising the steps of:

receiving at least one ECG signal;
analyzing the ECG signal to provide features and/or identify at least one episode and/or event, wherein an episode is a segment of the ECG signal defined by a starting time, a duration and a label obtained during the analysis of the ECG signal and an event is a strip of the ECG signal of predefined duration defined by a starting time and a label obtained during the analysis of the ECG signal; and
displaying a multiple field display.

The multiple field display includes at least:
a main plot, being a global view of a graphic representation of the ECG signal in a first time window;
a local view of a graphic representation of the ECG signal in a second time window, where the first time window comprises the second time window;
an intermediate view of a graphic representation of the ECG signal in a third time window, wherein the third time window comprises the second time window and has a duration comprised between the duration of the first time window and the duration of the second time window; and
at least one interactive means being a cursor capable of selecting a reference time on the main plot by sliding on a time bar, said time bar comprising visual means highlighting on the time bar time segments corresponding to episodes and/or events.

Such a multiple field display advantageously presents to physicians ECG data in a format that includes relevant local views and a global view, which together provide contextual information improving diagnostic accuracy. In particular, this has the advantage of providing in the field of view of the user at least three representations of the ECG signal at different time scales, allowing the user to access global information in a long time window in the main plot and simultaneously detailed information concerning the ECG signal in the shorter duration second and third time windows.

The short duration view provides a classical view of an ECG at traditional recording speed in a manner that is known to physicians. The global view or intermediate view provide an intermediate/lower resolution view. This combination of different time scale plots leads the user to an easier and faster interpretation of the ECG signal. Advantageously, the events and episodes of interest detected during the analysis step provide precious information that is visualized with highlighting means on the time bar. These visual landmarks on the time bar allow the user to target the desired time segments by sliding the cursor on the time bar, which causes a simultaneous adaptation of the graphic representation of the ECG signal in the global view, intermediate view and local view.

According to one embodiment, the graphic representation of the ECG signal, in the main plot, local view and intermediate view, is a strip of ECG signal or a plot of features associated to the ECG signal as a function of time.

According to one embodiment, the multiple field display includes directly editable information for the analysis of the electrocardiogram.

According to one embodiment, the multiple field display comprises at least one interactive means configured to select at least one strip of ECG signal and/or at least one of the directly editable information.

Such interactive means advantageously allow the user to select editable information of his choice in order to generate a clinical report comprising the most pertinent information concerning the patient.

According to one embodiment, the interactive means are further configured to execute at least one of the following actions:
zooming in and out of the main plot;
defining a new episode by selecting a time window on the main plot; and
highlighting on the main plot the presence of events and/or episodes associated to at least one label.

The highlighting of events and episodes of interest on the main plot (i.e. on a multiple-day representation of the ECG signal) advantageously guides the user, so to allow an easier and more efficient navigation of the graphical representation of the ECG signal. By selecting one of the highlighted events and episodes in the main plot, the related graphic representation of ECG signal in the intermediate view and local view is automatically displayed. This advantageously provides in a click detailed views of the ECG signal associated to the global pattern that the user had selected on the main plot thanks to the guidance of the highlighting of events and episodes.

According to one embodiment, in the multiple field display is further displayed at least one ECG strip associated to one episode and/or at least one ECG segment associated to one event.

According to one embodiment, the analysis step comprises a step of delineation of the ECG signal and a step of classification of the ECG segment, on the basis of the results of the delineation step, in order to identify the episodes and/or the events.

The delineation step and classification step provide useful information for the users (e.g. physicians) allowing a better evaluation of the health condition of a patient.

According to one embodiment, the features provided from the analysis of the ECG signal include any measurement derived from the ECG signal during the analysis step and the labels associated by the classification step to the ECG segments or strips are associated to an abnormality in the ECG signal corresponding to a clinical condition or signal noise.

According to one embodiment, the at least one ECG signal is a holter.

According to another aspect, the present invention relates to an interactive electrocardiogram analysis system comprising a remote server, having access to a medical database comprising at least one ECG signal recording of a patient and enabling the analysis and interactive displaying of said ECG signal recording, and at least one computer device, capable of communicating at least temporarily with the remote server to exchange ECG data and displayable information, wherein the remote server comprises:
- a processor;
- a memory;
- a data exchange module; and
- an analysis module, configured to analyze the ECG signal to provide features and/or identify at least one episode and/or event in the ECG signal;
- a graphical representation module, configured to generate a graphical representation of the ECG signal;
- a window generation module, configured to format into a plurality of successive fixed display windows for an interactive visualization of a multiple field display on a display screen; said multiple field display including at least:
  - a main plot, being a global view of a graphic representation of the ECG signal in a first time window;
  - a local view of a graphic representation of the ECG signal in a second time window, where the first time window comprises the second time window;
  - an intermediate view of a graphic representation of the ECG signal in a third time window, where the third time window comprises the second time window and has a duration comprised between the duration of the first time window and the duration of the second time window; and
  - at least one interactive means, being a cursor configured to select a reference time on the main plot by sliding on a time bar, said time bar comprising visual means highlighting on the time bar time segments corresponding to episodes and/or events;
- an interaction module, configured to control the interactive means enabling interactive visualization of the display windows of the multiple field display for the exploration along time of the graphic representations of the ECG signal in the main plot, the local view and the intermediate view;

and wherein the at least one computer device comprises a display screen, a microprocessor, a memory and a data exchange module.

According to one embodiment, the system further comprises an editing module, configured to edit a report comprising at least one selected ECG strip and/or ECG segment.

According to another aspect, the present invention relates to a computer program comprising instructions which, executed by a computer, cause the computer to carry out the steps of the method according to any one of the embodiments described hereabove.

According to yet another aspect, the present invention relates to a computer readable medium comprising instructions which, when executed by a computer, cause the computer to carry out the steps of the method according to any one of the embodiments described hereabove.

DETAILED DESCRIPTION

The following detailed description will be better understood when read in conjunction with the drawings. For the purpose of illustrating, the method is shown in the preferred embodiments. It should be understood, however that the application is not limited to the precise arrangements, structures, features, embodiments, and aspect shown.

This invention relates to a computer-implemented method for electrocardiogram analysis. Such an analysis aims at providing a detailed and precise account of the abnormalities found in the analyzed ECG. The method therefore provides a way to find, select and save abnormalities, and to gather them in a report.

According to one embodiment, in order to assist the user in this analysis the method comprises the steps of:
- receiving at least one ECG signal;
- performing an automated analysis of the ECG signal using at least one algorithm to provide features and/or descriptors associated with ECG signal portions which are presented to the user in the next step;
- displaying at least one graphic representation of the ECG signal and/or at least one features and/or at least one strip of ECG signal and/or at least one descriptor, in a multiple-field display, in an interactive way, so that the user can modify and save the analysis provided by the second step of the method.

According to one embodiment, the displaying step comprises interactive means configured to interactively display, in a multiple field display, the graphic representation of the ECG signal and/or the features and/or the strip(s) of ECG signal and/or the descriptor(s) associated to portions of the ECG signal.

According to one embodiment, said interactive means includes means for the selection of strips containing relevant information.

According to one embodiment, the display includes directly editable relevant information for electrocardiogram analysis, including preselected strips associated to an episode where a label is present.

According to one embodiment, the at least one ECG signal is a holter.

According to one embodiment, the analysis step comprises a first phase of delineation of the ECG signal and a second phase of classification of the ECG segment, on the basis of the results of the delineation step, in order to identify the episodes and/or the events. The step of delineation enables the computation of heartbeat-level features such as RR intervals, heart rate, maximum heart rate and the like. Such beat level features are then used for the aggregated representation displayed in the main plot.

According to one embodiment, a label provides a specification of a characteristic of the ECG signal at a time point or in a time window. In particular, a label can be put on a time segment of the signal as the rhythm abnormality associated with this time segment, such as atrial fibrillation, ventricular tachycardia, sinus tachycardia. In one example, the label may be obtained by automated analysis of the ECG signal using classification algorithms allowing for example to distinguish between different cardiac abnormalities. In one example, a label may be attributed to a time point or a time window when a calculated variable exceeds a certain predefined threshold. For instance, a time window may be labeled as noise if the noise-to-signal ratio exceeds a threshold; a time window may be labeled as sinus tachycardia if the heart rate exceeds a specific threshold. A label may be associated to a string of characters briefly describing the characteristic of the ECG signal to which it is associated.

According to one embodiment, the features include any measurement derived from the signal during the analysis step. By means of non-limiting example the features may be the number of heart beats, the heart rate, the heart rate frequency, the R-R intervals and combinations thereof.

According to one embodiment, the descriptor includes a label associated to an episode or an event.

According to one embodiment, the reception step further comprises the reception of electronic medical record data. In one example, said medical record data are retrieved from a medical database or received in real time from a holter monitor worn by a user.

According to one embodiment, the patient has the possibility to tag, by interacting with the ECG monitoring device, a time window of predefined duration in the ECG recording, which generates the definition of a new event labelled as "patient alert". Notably, the patient may interact with the ECG monitoring device, for example by pushing an alert button, in concomitance with a feeling of atypical behavior of the heart. In one example, the beginning of the event time window is chosen as a time point preceding the moment at which the patient has pushed the alert button, in particular up until 10 minutes before the time point at which the patient has pushed the alert button.

According to one embodiment, the analysis includes a preliminary step of processing, for example for denoising of the ECG signal or extraction of a set of measurements from the ECG waveforms.

According to one embodiment, the multiple field display includes at least two display fields.

According to another embodiment, the multiple field display includes at least one interactive graphic representation of the ECG signal in a variable length time window. The length of the time window may variate from 1 second to a few weeks, and preferably the length of the time window may be of 1 sec, 2 sec, 3 sec, 4 sec, 5 sec, 6 sec, 7 sec, 8 sec, 9 sec, 10 sec, 15 sec, 20 sec, 25 sec, 30 sec, 35 sec, 40 sec, 45 sec, 50 sec, 55 sec, 60 sec, 1.5 min, 2 min, 2.5 min, 3 min, 3.5 min, 4 min, 4.5 min, 5 min, 5.5 min, 6 min, 6.5 min, 7 min, 7.5 min, 8 min, 8.5 min, 9 min, 9.5 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, 1 h, 6 h, 12 h, 18 h, 24 h, 30 h, 36 h, 42 h, 48 h, 54 h, 60 h, 66 h, 72 h, 78 h, 84 h, 90 h, 96 h, 102 h, 108 h, 114 h, 120 h, 126 h, 132 h, 138 h, 144 h, 150 h, 156 h, 162 h, 168 h, 174 h, 180 h, 186 h, 192 h, 198 h, 204 h, 210 h, 216 h, 222 h, 228 h, 234, 240 h, 246 h, 252 h, 258 h, 264 h, 270 h, 276 h, 282 h, 288 h, 294 h, 300 h, 306 h, 312 h, 318 h, 324 h, 330 h, 336 h, 342 h, 348 h, 354 h, 360 h, 366 h, 372 h, 378 h, 384 h, 390 h, 396 h, 402 h, 408 h, 414 h, 420 h, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

According to one embodiment, the multiple field display includes at least a graphic representation of a global view of the ECG signal in a first time window and a local view comprising related ECG data in a second time window, where the first time window comprises the second time window. This has the advantage of providing in the field of view of the user two representations of the ECG signal at different time scale allowing the user to access global information in a larger time window in the main plot and detailed information in a shorter time window in the first ECG strip.

According to one embodiment, the multiple field display includes, on a first side of the display, a main plot and at least one ECG strip, and, on the second side of the display, at least one ECG strip.

According to one embodiment, the main plot is graphic representation of the ECG signal. The main plot may be a heart rate trend plot, representing the instantaneous heart rate (HR) as function of time. The instantaneous heart rate is calculated as a mean of the heart rate over a fixed duration, the duration being for instance two, five or ten seconds. In this configuration, the HR trend plot draws a line passing by values of the instantaneous heart rate computed, for instance, every two, five or ten seconds.

According to one embodiment, the main plot is an interactive graphic representation of the whole ECG signal comprising a cursor capable of selecting a reference time on a temporal axis of the main plot.

According to one embodiment, the multiple field display includes on a first side of the display, the main plot, a first ECG strip in a first time window comprising the reference time selected by the cursor in the main plot, and a second ECG strip having a broader second time window compared to the first ECG strip and comprising said first ECG strip. The use of this second ECG strip is to provide a small context window around the first ECG strip and provide an intermediate view of the ECG signal. Advantageously, this intermediate view of ECG signal displayed simultaneously to the global view of the main plot allow a physician to comparatively view heart rate context and patterns of behavior prior to and after a clinically meaningful event and/or episode (i.e. arrhythmia), patient concern or other indicia, thereby enhancing diagnostic specificity of cardiac rhythm disorders and providing physiological context to improve diagnostic ability.

According to one embodiment, the second ECG strip comprises a second cursor and the second ECG strip is used as scrollbar for said second cursor. This provides an additional interactive means allowing the user to choose a reference time to be visualized in the main plot an in the local view. In this embodiment, moving the second cursor causes a displacement of the cursor on the time bar of the main plot.

According to one embodiment, the multiple field display includes at least one interactive graphic object associated to a label which is configured to activate the displaying on the main plot of graphical means indicating the presence of at least one episode or event labelled with the label associated to the interactive graphic object itself. Said interactive graphical object may have the aspect of a button, and in the present description will be referred to as label button. The multiple field display may comprise as many label buttons as the number of types of labels that the computer-implemented method is configured to calculate. Labels activated by these buttons may be, but are not limited to, heart rhythm abnormalities, examples of which are atrial fibrillation, atrio-ventricular block, ventricular tachycardia and premature heart beats, such as premature supraventricular complexes and premature ventricular complexes. In one example, the graphical means indicating the presence of an episode may be a change in the color of a segment of the main plot, in which case the episode is indicated by a band of color extending over the time window associated to the episode, or a change in the color of the points that the main plot are comprised in the time window associated to the episode. In this example, the color is associated to a type of beat label, such as premature ventricular complex (PVC) or premature supraventricular complex (PSVC). Both color bands and points can be hidden by clicking on related buttons in a legend displayed in the multiple field display. In a second example, the graphical means highlighting one event may be a change of color of the time point associated to the event. The highlighting of events and episodes of interest through the selection of a desired label button associated to a specific characteristic of the ECG signal allows advantageously the user to easily and rapidly identify, on a multiple days representation of the ECG signal, the few segments of ECG the user is invited to look closer at (such as episodes of arrhythmias), and easily navigate the context of both short and long episodes.

The foregoing approach aids the cardiologist's diagnostic job by facilitating presentation of ECG-based background information prior to and after the identified event.

According to one embodiment, on the second side of the display is displayed at least one ECG strip extracted from at least one episode, the episode corresponding to a selected label.

According to one embodiment, the interactive means are configured for the exploration of said multiplot display field, where the exploration comprises at least one of the following:
1. selecting a reference time along a main plot temporal axis;
2. zooming in and out the main plot;
3. exploring the graphical representation of the EGC signal and/or ECG features along the temporal axis in a time interval corresponding to the full recording time;
4. defining a new episode by selecting a time window in the main plot; and/or
5. selecting at least one label button for showing episodes associated to at least one descriptor.

According to one embodiment, the first ECG strip in the first side of the display further comprises a second interactive means capable of moving the time window of the ECG strip, and accordingly the reference time on the main plot, so that the reference time is comprised in the time window.

According to one embodiment, the at least one ECG strip in the second side of the display is an episode plot representing an extract of an episode. The advantage displaying the episode plot, in addition to the main plot and the ECG strip plot, is that of providing in the field of view of the user multiple representations of the ECG signal at different time scales. This allows the user to access global information in a larger time window in the main plot and detailed information in a shorter time window in the first ECG strip and in the episode plots. This combination of different time scale plots leads the user to an easier and faster interpretation of the ECG signal, as users can navigate on the main plot at different time points around the episode and analyze the corresponding signal on the strip plot to confirm the diagnosis or comment the episode.

According to one embodiment, the episode plots, selected by a label button, comprise a strip of the ECG extracted from at least one portion of ECG signal classified as episode with said label.

According to one embodiment, the second display side comprises a third interactive means to select at least one representative episode plot and delete at least one non-representative episode plots.

According to an alternative embodiment, the second display side comprises in each episode plot a third interactive means to select the episode associated to episode plot to be added to an editable report and a fourth interactive means to delete the episode of the episode plot from the second display side.

According to one embodiment, the method further comprises interactive means configured to generate one episode plot when a new episode is defined, and preferably display the episode plot in the second display side.

According to one embodiment, the third interactive means are further configured to automatically move the cursor on the main plot to relevant time points, associated to an episode plot. A relevant episode may be, by means of on limiting example, the beginning of an episode or the end of an episode.

The episode plots in the second side of the multiple field display are used to represent simultaneously one or more ECG strip that may have a variable duration. In order to allow an easy and uniform representation of the ECG strip in the episode plot, all episode plot having ECG strips of duration superior to a predefined threshold, for example 10 seconds, may display on a segment of the ECG strip in a predefined time window. According to one embodiment, an episode plot which represents an ECG strip registered on a time interval longer than 10 seconds or a few tens of seconds further comprises interactive means configured to represent in the episode plot a segment of the ECG strip in a predefined time window starting from the time of beginning of the episode. Said predefined time window may for example lasts 10 to 60 seconds.

According to one embodiment, the method of the present invention further comprises a step of calculating a temporal burden as the ratio between the summation of all time periods associated to a same label and the total time of ECG signal acquisition.

According to one embodiment, the method of the present invention further comprises a step of calculating a count burden for events, such as for instance premature ventricular complexes and premature atrial complexes, as the ratio between the counts associated to a type of event and the total of heart beats measured in the whole of ECG signal. According to an alternative embodiment, the count burden can be calculated directly as the number of counts of events such as for instance premature ventricular complexes and premature atrial complexes.

According to one embodiment, the method of the present invention further comprises the step of editing a report comprising at least one episode plot, a selection of information extracted from the electronic medical record data and the burden.

According to one embodiment, at least one field of the multiple field display is a R-R plot.

The invention also relates to an interactive electrocardiogram analysis system for implementing the method for ECG analysis, according to embodiments described here above. Said system enables the analysis and interactive displaying of said ECG signal recordings.

According to one embodiment, the interactive electrocardiogram analysis system comprises a remote server and at least one computer device. The remote server may access to a medical database comprising at least ECG signal recordings of patients. The at least one computer device, is capable of communicating at least temporarily with the remote server to exchange ECG data and displayable information.

According to one embodiment, the remote server comprises:
  at least one processor;
  at least one working memory;
  a data exchange module; and
  an analysis module, to analyze the ECG signal to provide features and/or descriptors associated to ECG signal portions.

According to one embodiment, the at least one computer device comprises:
  a display screen;
  at least one microprocessor;
  at least one working memory;
  a data exchange module;

a display window generation module, enabling the graphical representation of the ECG signal, features and/or descriptors to be formatted into a plurality of successive fixed display windows, comprising at least one portion of the graphical representations, and displaying on the display screen;

an interaction module, controlling the interactive means enabling the interactive visualization of the display window and allowing the user to select the display window comprising the representative episode plots; and an editing module, editing a report comprising at least one of the selected episode plots.

According to one embodiment, the visualization of new display windows is performed in real time.

According to one embodiment, the remote server further comprises a graphical representation module, generating a graphical representation of the ECG signal, ECG features and/or descriptors to transfer to the computer device.

A second aspect of the present invention relates to a computer-implemented method for electrocardiogram analysis, the method comprising:

receiving at least one ECG signal;

analyzing the ECG signal, at least through delineation and classification, in order to define episodes in the ECG signal by associating time slots to labels; and interactively displaying representation of the ECG signal in the form of at least three distinct display fields.

According to one embodiment, the interactively displaying method comprises:

at least one main plot, comprising a graphical representation of the ECG signal or at least one feature derived from the ECG signal as a function of time and a first interactive means configured for navigation of said graphical representation, where navigation comprises:
  selecting a reference time along a main plot temporal axis;
  zooming in and out the main plot;
  exploring the graphical representation along the temporal axis along a time interval corresponding to the full recording time;
  selecting at least one label button for showing episodes associated to at least one label;

at least one ECG strip plot, comprising:
  a graphical representation of a strip of ECG signal and/or at least a feature derived from the ECG signal as a function of time, where said ECG strip graphical representation is displayed for a fixed time window comprising the reference time selected on the main plot;
  a second interactive means capable of moving the time window of the strip graphical representation and accordingly the reference time on the main plot so to be comprised in the time window;

at least one episode plot, selected by a label button, and comprises a strip of the ECG extracted from at least one portion of ECG signal classified as episode with said label.

According to one embodiment, the at least one ECG signal is a Holter.

According to one embodiment, the reception step further comprises the reception of electronic medical record data.

According to one embodiment of the second aspect of the invention, the analysis includes a preliminary step of processing, for example for denoising or extraction of a set of measurements of the ECG waveforms.

According to one embodiment, the features include any measurement derived from the signal during the analysis step. By means of non-limiting example the features may be the number of heart beats, the heart rate, RR intervals, the heart rate frequency and combinations thereof.

According to one embodiment, the label is associated to an abnormality in the ECG signal corresponding to a clinical condition or signal noise.

According to one embodiment, the analysis step comprises the calculation of a noise assessment for all strips comprised in the signal.

According to one embodiment, the first interactive means further comprises selecting a time interval in the main plot and defining said time interval as a new episode.

According to one embodiment, the method according to the second aspect of the present invention further comprises a third interactive means to select at least one representative episode plot and delete at least one non-representative episode plots.

According to one embodiment, the method according to the second aspect of the present invention further comprises a step of calculating burden as the ratio between the summation of all time periods associated to a same label and the total time of ECG signal acquisition.

According to one embodiment, the method according to the second aspect of the present invention further comprises a step of editing a report comprising the selected representative episode plot, some electronic medical record data, a description of the general characteristic of the signal and the burden.

According to one embodiment, at least one of the multiple field display is a R-R plot or mean heart rate plot.

According to one embodiment, the first interactive means allow to select a label button and visualize all episodes corresponding to the label on the main plot, and display at the same time at least one episode plot corresponding to each of the labelled episodes, and sorting the episode plot by duration, beginning time, heart rate or relevance criteria.

The invention also relates to an interactive electrocardiogram analysis system for implementing the method according to here above embodiments related to the second aspect of the present invention. Said system enables the analysis and interactive displaying of said ECG signal recordings.

The interactive electrocardiogram analysis system comprises a remote server and at least one computer device. The remote server has access to a medical database comprising at least ECG signal recordings of patients. The at least one computer device, is capable of communicating at least temporarily with the remote server to exchange ECG data and displayable information.

According to one embodiment, the remote server comprises:
  at least one processor;
  at least one working memory;
  a data exchange module; and
  an analysis module, to analyze the ECG signal to provide features and/or descriptors associated to ECG signal portions.

According to one embodiment, the at least one computer device comprises:
  a display screen;
  at least one microprocessor;
  at least one working memory;
  a data exchange module;
  a display window generation module, enabling the graphical representation of the ECG signal, features and/or descriptors to be formatted into a plurality of successive fixed display window, comprising at least a portion of the graphical representations, and displaying on the display screen;

an interaction module, controlling the interactive means enabling the interactive visualization of the display window and allowing the user to select the display window comprising the representative episode plots; and an editing module, editing a report comprising at least one of the selected episode plot.

According to one embodiment, the visualization of new display windows is in real time.

According to one embodiment, the remote server further comprises a graphical representation module, generating a graphical representation of the ECG signal, ECG features and/or descriptors to transfer to the computer device.

Another aspect of the present invention relates to computer program product for the analysis of ECG signal to produce an interactive representation of multiple plots and allow the production of an editable report, said computer program product comprising instructions which, when the program is executed by a computer, cause the computer to automatically carry out the steps of the method according to any one of the embodiments described here above.

Yet another aspect of the present invention relates to a computer-readable storage medium comprising instructions which, when the program is executed by a computer, cause the computer to carry out the steps of the computer-implemented method according to any one of the embodiments described here above. According to one embodiment, the computer-readable storage medium is a non-transitory computer-readable storage medium.

Computer programs implementing the method of the present embodiments can commonly be distributed to users on a distribution computer-readable storage medium such as, but not limited to, an SD card, an external storage device, a microchip, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While various embodiments have been described and illustrated, the detailed description is not to be construed as being limited hereto. Various modifications can be made to the embodiments by those skilled in the art without departing from the true spirit and scope of the disclosure as defined by the claims.

ILLUSTRATIVE EMBODIMENTS OF THE INVENTION

Figure 1:
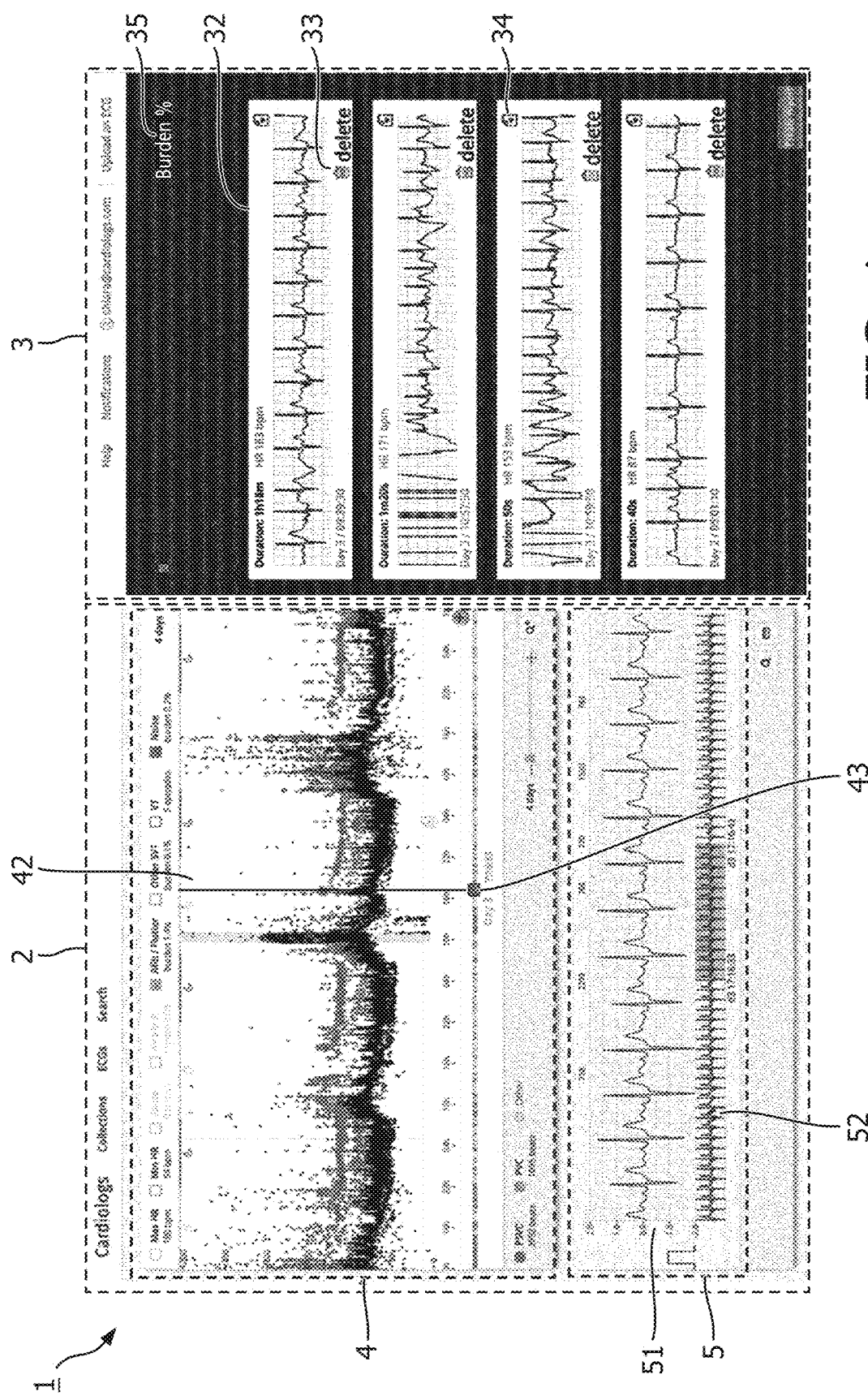
FIG. 1 is a screenshot of the interface where in the main plot are highlighted signal segments corresponding to atrial fibrillation by selecting the label button "Afib" and the episode plots on the right shows the strips associated to those highlighted atrial fibrillations episodes.
Figure 2:
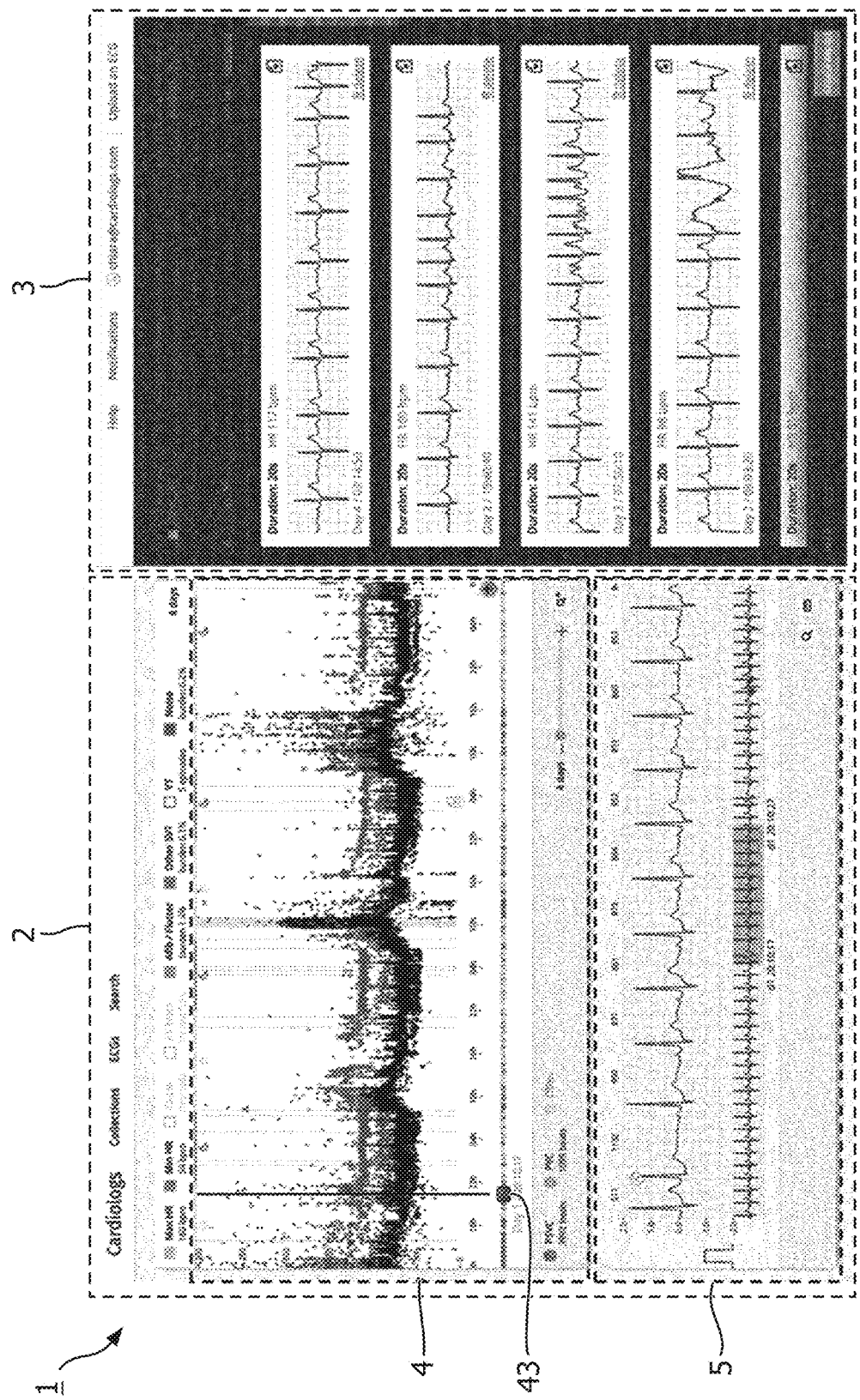
FIG. 2 is a screenshot of the interface where, in addition to the button "Afib", also the button "OtherSVT" is activated to show the episode plots comprised in episodes of supraventricular tachycardia and highlight the corresponding segment of signal in the main plot, the main plot being a R-R plot.

As shown in FIGS. 1 and 2, the computer implemented method of the present invention is configured to display a multiple field display 1. According to a first embodiment, the multiple field display 1 comprises a first side 2 and a second side 3.

The first side 2 comprises multiple sub-regions, notably a first graphic window 4 and a second graphic window 5.

The first graphic window 4 comprises a main plot 42 providing a global view of the ECG evolution in a first time window by means of a ECG's derived feature: the R-R interval plot. In this first embodiment, the time window has a duration of 24 hours, as shown by the time axis in abscissa.

The second side 3 of the multiple display plot 1 comprises multiple episode plots 32. Each episode plots 32 displays at least one segment of the ECG strip of the associated episode and strings of characters providing information concerning the duration (e.g. "Duration: 1 h 38 m") and the starting time of the episode (e.g. "Day 3/09:39:30"). Furthermore, each episode plot 32 comprises third interactive means 34 to select the corresponding ECG strip in order to add its graphical representation in the editable report. Each episode plot 32 further comprises a fourth interactive means 33 configured to allow the user to delete the episode plots where the associated ECG strip is not representative of the selected label. The second side 3 further comprises a string of characters 35 providing the burden value for the events and/or episodes associated to the selected label.

Figure 7:
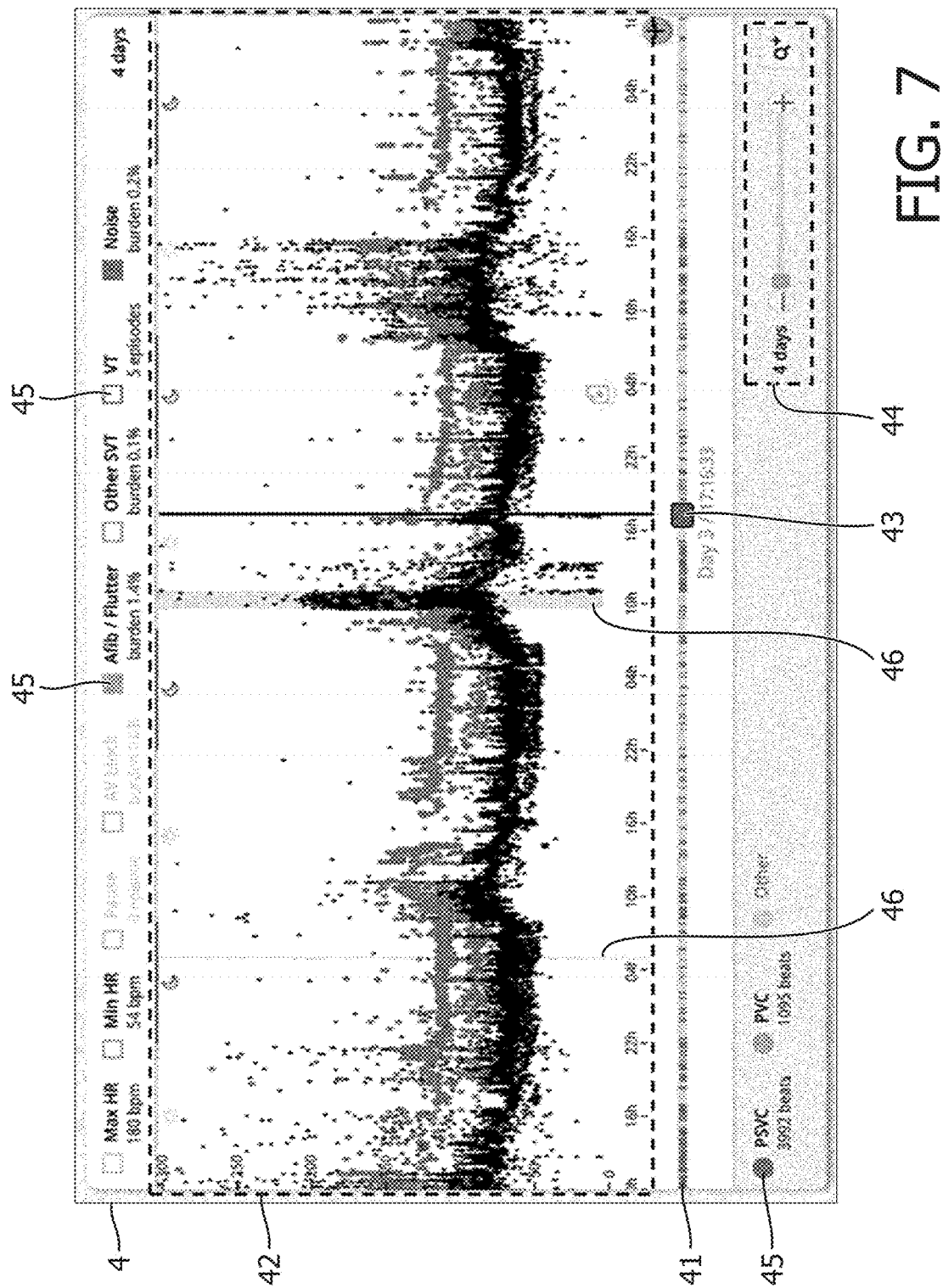
FIG. 7 is a zoom in of the first graphic window of the interface screenshot represented in FIG. 1.

FIG. 7 represents a zoom in FIG. 1 in correspondence with the first graphic window 4. As shown in FIG. 7, in the upper region the first graphic window 4 comprises multiple label button 45. Each label button has, displayed in its proximity, a string describing the label to which it is associated and supplementary information, for example the burden value for the related label. Each label button 45 is associated to a color so that, when a label button 45 is selected by the user, the graphical means 46 are displayed on the main plot 42 in order to visually indicate the presence of the episodes and/or events associated to the selected label. This provides visual references to the user allowing an easy identification of a specific category of events and/or episodes. According to this embodiment, the first graphic window 4 comprises label buttons 45 associated to the beat label PVC (premature ventricular complex) and PSVC (premature supraventricular complex). The points in the main plot 42 comprised in the time window associated to the beat label PVC and PSVC are colored, as shown in FIG. 7 by the presence of points of color different from black.

The first graphic window 4 further comprises, parallel to the time axis of the main plot 42, a temporal bar 41, also called temporal axis in the description above. Said temporal bar 41 provides a linear representation of the total ECG acquisition time wherein the time periods associated to episodes or the time points associated to events are represented as colored segments. In particular, in this embodiment the darker grey zones on the temporal bar 41 correspond to time periods of noisy signal (i.e. when the signal is too artifacted and the analysis algorithm cannot propose a delineation and proper detection). The first graphic window 4 further comprises an interactive cursor 43 configured to move along the temporal bar 41 in other to allow a navigation of the main plot 42 in time on the total acquisition time of the ECG signal. The color spots on the time bar 41, indicating the presence of episodes and events, guide the user in the choice of the time period to be observed in the main plot 42 and give an easy landmark for the displacement of the cursor 43.

In the right bottom corner, the first graphic window comprises the second interactive means 44 configured to produce a zoom in and out on the main plot.

FIGS. 1 and 2 show as well that the second graphic window 5 comprises a first ECG strip 51 in a second time window starting at the time point selected by the cursor 43. The second graphic window 5 further comprises a second ECG strip 52 in a third time window. Said third time window is larger than the second time window and totally comprises the second time window.

Figure 3A:
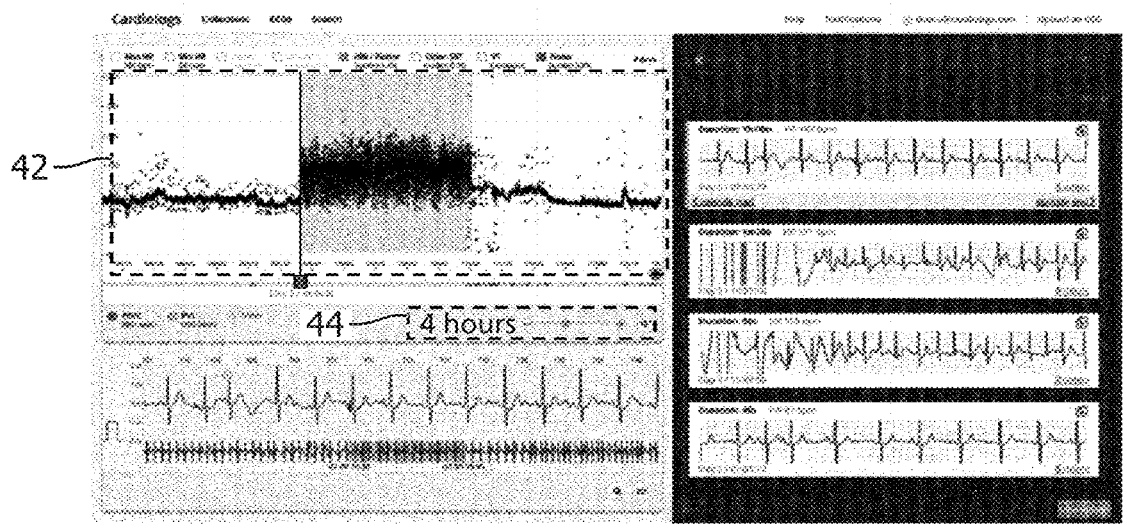
FIG. 3 comprises two screenshots of the graphical interface where the main plot of FIG. 3B is a zoom of the main plot of FIG. 3A in order to allow better visualization of the highlighted portion of signal.
Figure 3B:
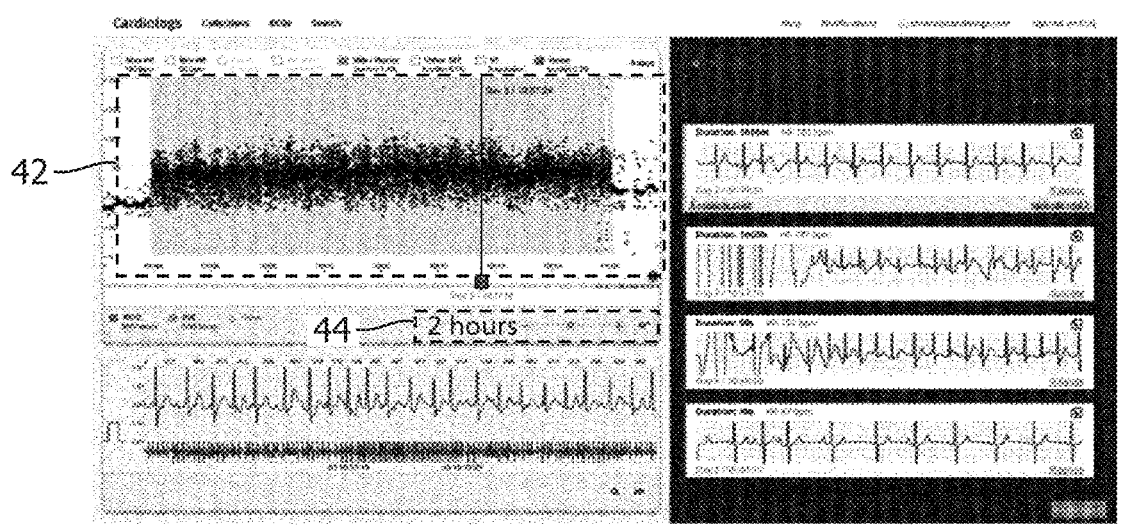

FIGS. 3A and 3B show the effect of the user interaction with the second interactive means 44, which produces a zoom in of the main plot 42. Indeed, the main plot in FIG. 3B is a zoom in of the main plot shown in FIG. 3A.

Figure 4A:
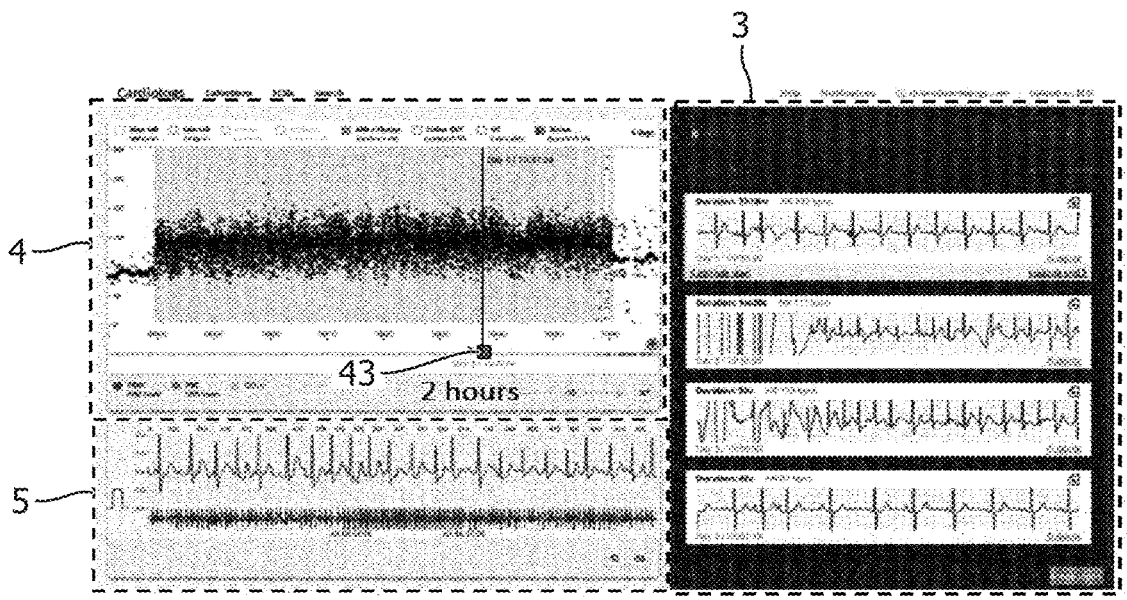
FIG. 4 comprises two screenshots of the graphical interface showing a main plot where the cursor used to select the reference time has been interactively moved from one initial position (FIG. 4A) to a new position (FIG. 4B), thus modifying the strip represented in the strip plot thereof.
Figure 4B:
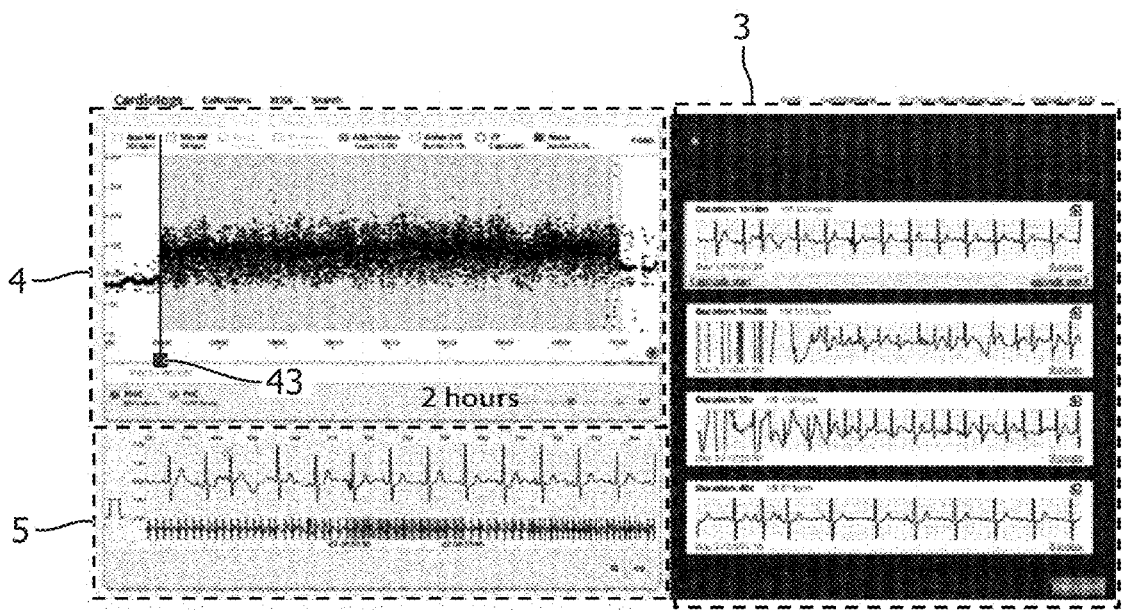

FIGS. 4A and 4B show a main plot 42 displaying the same R-R plot in a same time window while the cursor 43 is positioned on the time bar 41 in correspondence of two different time points. Therefore, the first ECG strip and the second ECG strip represented in the second graphic window 5 in FIGS. 4A and 4B are not the same.

Figure 5:
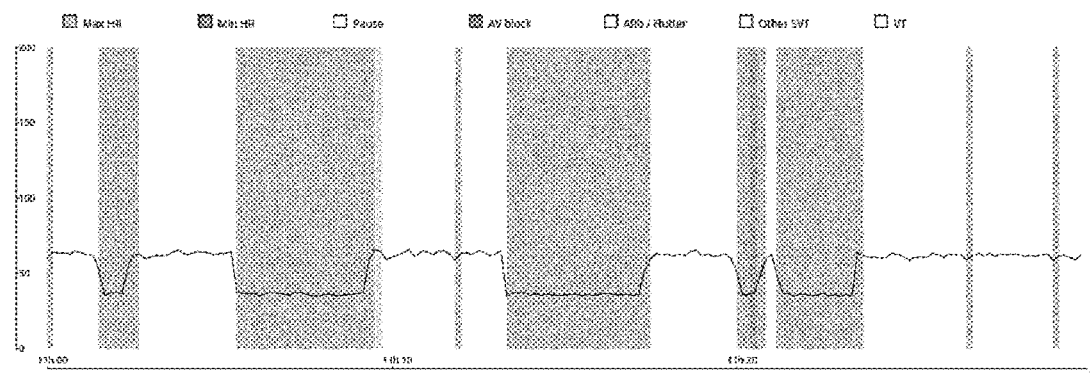
FIGS. 5 and 6 are an example of a first and a second page of a report edited according to a method and a system of the present invention.

According to the embodiment shown in FIG. 5, in the first page of the report edited with the method of the present invention is represented a table comprising information relative to the patient and to the physician following him. This first page further comprises graphical representation of ECG features, notably an R-R plot, in a user defined time window. Said time window is usually chosen in order to comprise episodes and/or events of interest. The first report page further comprises information concerning the ECG recording and extracted features (i.e. duration of the recording, minimum, maximum and average heart rate, etc.).

Figure 6:
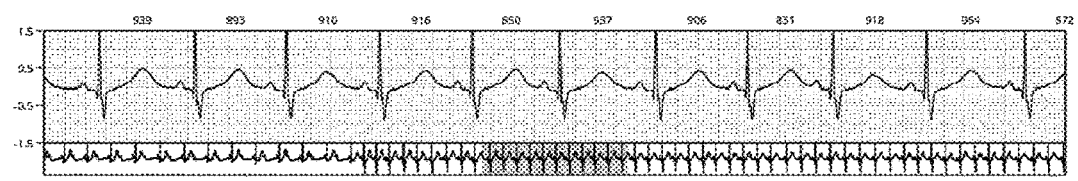
Figure 6:
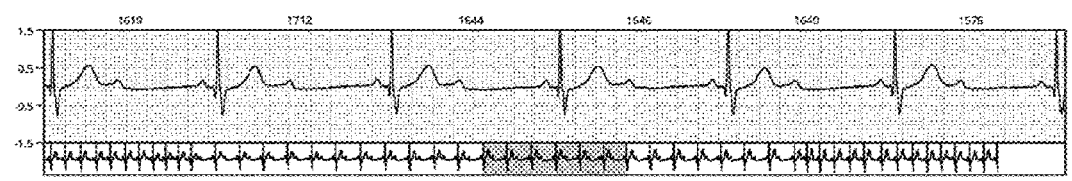
Figure 6:
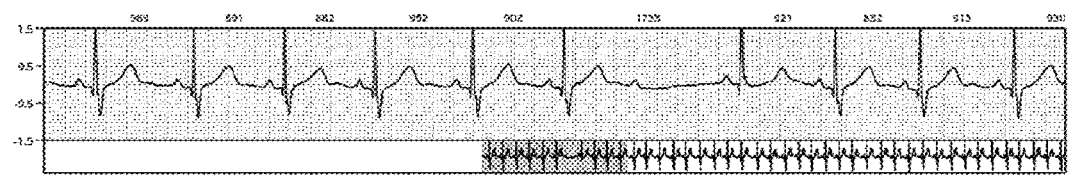
Figure 6:
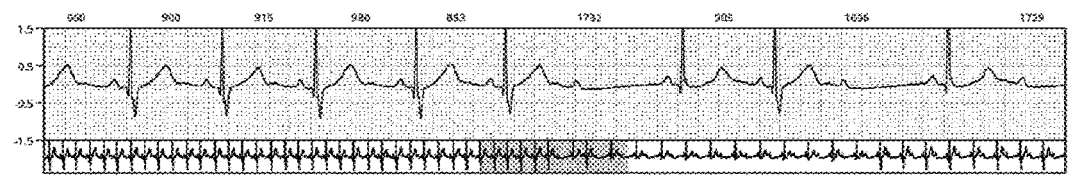

FIG. 6 shows the second page of the report according to one embodiment, wherein the ECG strips previously selected by the user are displayed with the related relevant associated metrics and comment as added by the user.

Figure 8:
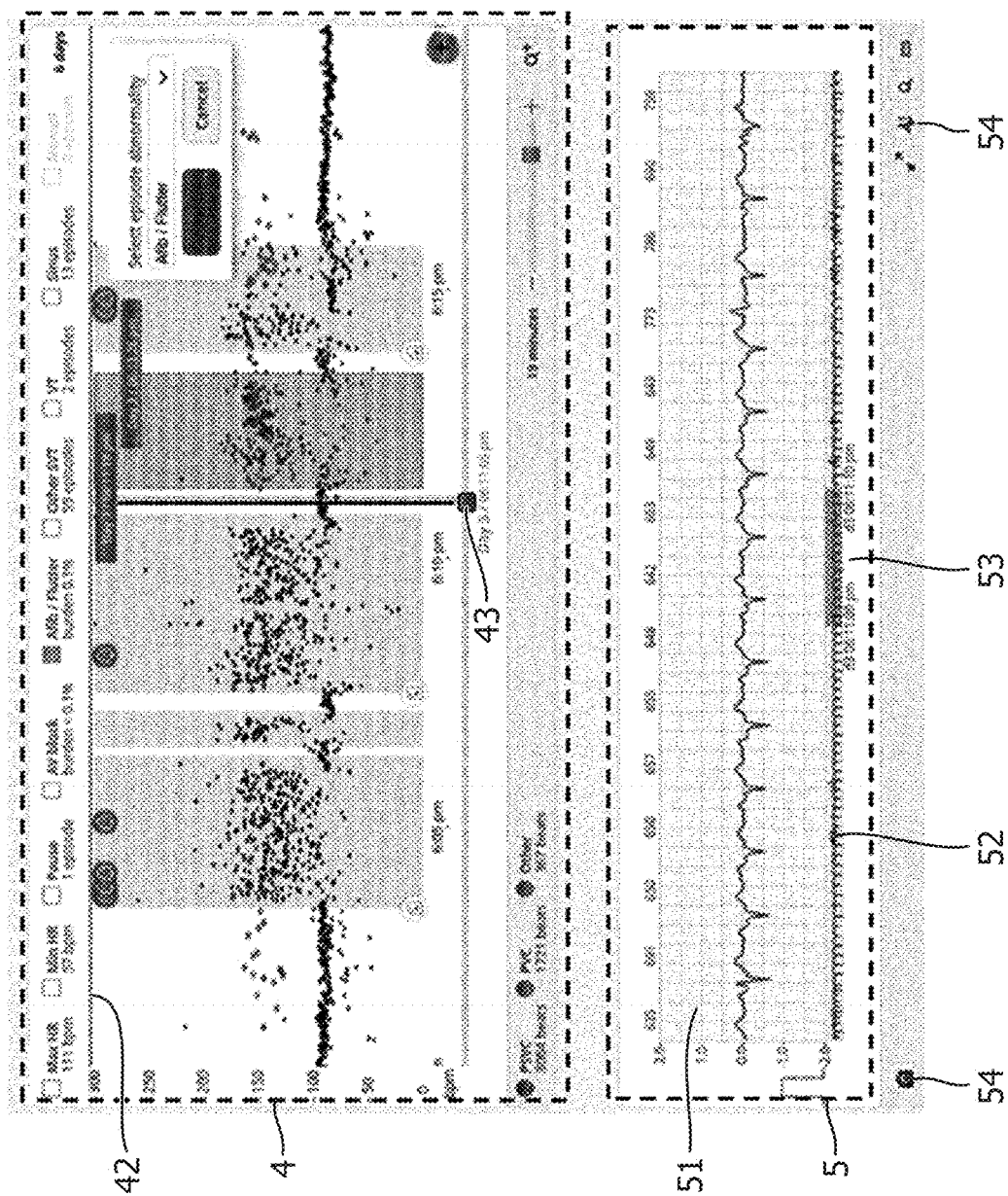
FIG. 8 is a zoom in of the first side of the multiple field display during the action of defining a new event.

According to the embodiment shown in FIG. 8, a new episode is defined using interactive means allowing the interaction of the user with the main plot. This interactive means are configured to select on the main plot a starting time point (visualized on the main plot: "Day 3/06:11:18 pm") and an end time point (visualized on the main plot: "Day 3/06:13:26 pm"). The interaction means are further configured to associate the new time window, defined from the starting time point and end time point, to one predefined label or a user customized label.

According to the embodiment of FIG. 8, the multiple field display comprises additional interactive means 54, visualized as small icons. Such interactive means allow for example to take an image of the ECG signal represented in the first ECG strip 51, which may be eventually added to the editable report, or to modify the voltage scale of the y-axis of the first ECG strip 51, or to measure the distance between the R waves visualized in the first ECG strip 51 and the like. According to this embodiment, the second ECG strip 52 is a scrollbar comprising a second cursor 53. Sliding second cursor 53 along second ECG strip 52 causes an automatic adaptation of the second time window of the first ECG strip 51.

Figure 9:
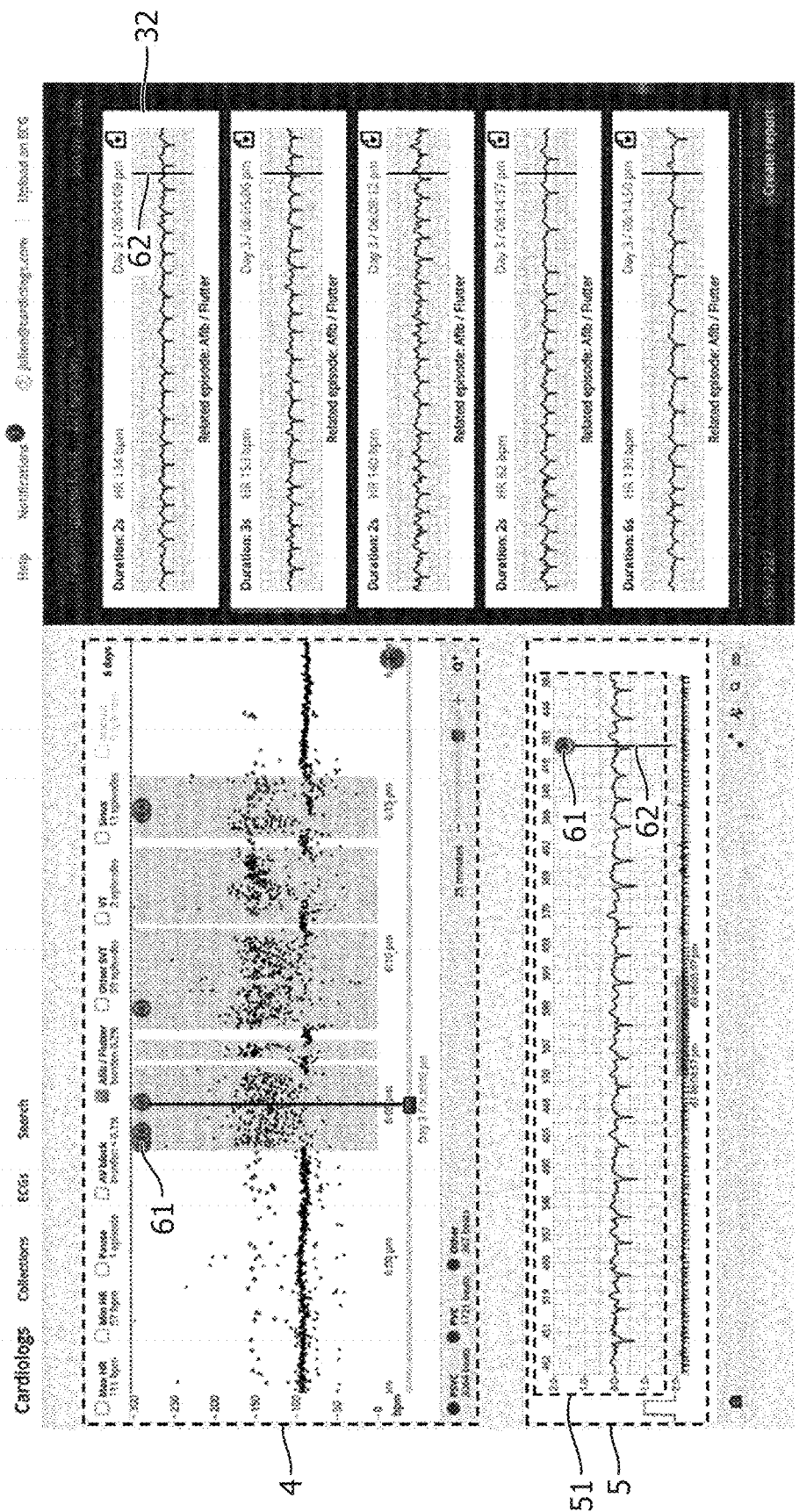
FIG. 9 is a screenshot of the multiple field display comprising multiple alert singulation means, according to one embodiment of the invention.

According to the embodiment shown in FIG. 9, the "patient alert" event generated by the patient, by interacting with the ECG monitoring device, are visualized as alert icons 61 in the main plot 42 and the first ECG strip 51. The time at which the alert is triggered by the patient is represented a vertical line 62 in the first ECG strip and in the episode plots 32.

The invention claimed is:

1. A computer-implemented method for electrocardiogram (ECG) analysis, the method comprising:
    receiving at least one ECG signal;
    analyzing the ECG signal to provide features and to identify a plurality of episodes and/or events, wherein an episode is a segment of the ECG signal defined by a starting time, an episode duration and a label obtained during the analysis of the ECG signal, and wherein an event is a strip of the ECG signal of predefined event duration defined by a starting time and a label obtained during the analysis of the ECG signal; and
    displaying a multiple field display, wherein the multiple field display includes at least:
    (a) a main plot being a global view of a graphic representation of the ECG signal in a first time window, wherein displaying the multiple field display comprises visually highlighting the plurality of episodes and/or events associated with the ECG signal on the main plot;
    (b) a local view of the graphic representation of the ECG signal in a second time window, wherein the first time window comprises the second time window;

(c) an intermediate view of the graphic representation of the ECG signal in a third time window, wherein the third time window comprises the second time window and has a duration between a duration of the first time window and a duration of the second time window;

(d) at least one episode plot of the graphic representation of the ECG signal corresponding to at least one episode and/or event of the plurality of episodes and/or events that is visually highlighted on the main plot, the at least one episode plot depicting the at least one episode and/or event; and (e) at least one interactive interface for selecting a timepoint on the main plot, wherein the at least one interactive interface comprises a cursor slidable on a time bar of the main plot, wherein sliding the cursor on the time bar causes simultaneous adaptation of the graphic representation of the ECG signal in the local view and the intermediate view based on a selected timepoint on the time bar corresponding to a position of the cursor on the time bar, and wherein selecting the at least one episode plot automatically moves the cursor on the time bar of the main plot to a timeframe at a beginning or an end of the at least one episode and/or event or between the beginning and the end of the at least one episode and/or event.

2. The computer-implemented method according to claim 1, wherein the graphic representation of the ECG signal, in the main plot, local view, intermediate view, and at least one episode plot is a strip of ECG signal or a plot of features associated to the ECG signal as a function of time.

3. The computer-implemented method according to claim 1, wherein the multiple field display includes directly editable information for the analysis of the ECG signal.

4. The computer-implemented method according to claim 3, wherein the at least one interactive interface is configured to select at least one strip of ECG signal and/or at least one of the directly editable information.

5. The computer-implemented method according to claim 1, wherein the interactive interface is further configured to execute at least one of:
   i. zooming in and out of the main plot;
   ii. defining a new episode by selecting a time window on the main plot; or
   iii. highlighting on the main plot events and/or episodes associated with at least one label.

6. The computer-implemented method according to claim 1, wherein the multiple field display further displays a plurality of episode plot comprising ECG strips each associated to one of the plurality of episodes and/or events.

7. The computer-implemented method according to claim 1, wherein the analyzing comprises delineating of the ECG signal and classifying of at least one ECG segment to identify the plurality of episodes and/or events.

8. The computer-implemented method according to claim 1, wherein the features provided from the analysis of the ECG signal include measurements derived from the ECG signal during the analyzing and the labels are associated with an abnormality in the ECG signal corresponding to a clinical condition or signal noise.

9. The computer-implemented method according to claim 1, wherein the at least one ECG signal is from a halter device.

10. An interactive electrocardiogram (ECG) analysis system comprising a remote server, having access to a medical database comprising at least one ECG signal of a patient and enabling analysis and interactive displaying of the ECG signal, and at least one computer device, configured to communicate at least temporarily with the remote server to exchange ECG data and displayable information, wherein at least one of the remote server or the at least one computer device is configured to:

analyze the ECG signal to provide features and/or identify a plurality of episodes and/or events in the ECG signal;

generate a graphical representation of the ECG signal;

generate a plurality of successive display windows for an interactive visualization of a multiple field display on a display screen, the multiple field display including at least:

(a) a main plot being a global view of a graphic representation of the ECG signal in a first time window, the main plot configured to visually highlight the plurality of episodes and/or events associated with the ECG signal;

(b) a local view of the graphic representation of the ECG signal in a second time window, wherein the first time window comprises the second time window;

(c) an intermediate view of the graphic representation of the ECG signal in a third time window, wherein the third time window comprises the second time window and has a duration between a duration of the first time window and a duration of the second time window;

(d) at least one episode plot of the graphic representation of the ECG signal corresponding to at least one episode and/or event of the plurality of episodes and/or events that is visually highlighted on the main plot, the at least one episode plot depicting the at least one episode and/or event; and (e) at least one interactive interface configured to select a timepoint on the main plot, wherein the at least one interactive interface comprises a slideable cursor on a time bar; and cause simultaneous adaptation of the graphic representation of the ECG signal in the local view and the intermediate view based on sliding of the cursor on the time bar to a selected timepoint on the time bar, and cause, in response to selecting the at least one episode plot of the graphic representation of the ECG signal, the cursor to automatically move on the time bar to a timeframe at a beginning or an end of the at least one episode and/or event, or between the beginning and the end of the at least one episode and/or event.

11. The interactive electrocardiogram analysis system according to claim 10, wherein the at least one of the remote server or the at least one computer device is further configured to edit a report comprising at least one selected ECG strip and/or ECG segment.

12. The interactive electrocardiogram analysis system according to claim 10, wherein the graphic representation of the ECG signal is a strip of ECG signal or a plot of features associated to the ECG signal as a function of time.

13. A computer program comprising instructions which, when executed by a computer, cause the computer to carry out the method according to claim 1.

14. A non-transitory computer readable medium comprising instructions which, when executed by a computer, cause the computer to carry out the method according to claim 1.

15. A computer-implemented method for electrocardiogram (ECG) analysis, the method comprising:

displaying a global view on a main plot of a graphic representation of at least one ECG signal in a first time window;

highlighting, on the main plot, a plurality of episodes and/or events identified by analyzing the at least one ECG signal;

displaying a local view of the graphic representation of the at least one ECG signal in a second time window, wherein the first time window comprises the second time window;

displaying an intermediate view of the graphic representation of the at least one ECG signal in a third time window, wherein the third time window comprises the second time window and has a duration between a duration of the first time window and a duration of the second time window;

displaying at least one episode plot of the graphic representation of the ECG signal corresponding to at least one episode and/or event of the plurality of episodes and/or events that is visually highlighted on the main plot, the at least one episode plot depicting the at least one episode and/or event;

selecting a timepoint on the main plot responsive to slidable interaction of a cursor slidable on a time bar;

causing simultaneous adaptation of the graphic representation of the at least one ECG signal in the local view and the intermediate view based on sliding of the cursor to a selected timepoint on the time bar; and causing, in response to selecting the at least one episode plot of the graphic representation of the ECG signal, the cursor to automatically move on the time bar to a timeframe at a beginning or an end of the at least one episode and/or event, or between the beginning and the end of the at least one episode and/or event.

16. The computer-implemented method of claim 15, further comprising:
delineating the at least one ECG signal; and
classifying the at least one ECG signal that has been delineated to identify the plurality of episodes and/or events.

17. The computer-implemented method of claim 16, further comprising labeling, based on the classifying, ECG segments of the at least one ECG signal that are associated with an abnormality in the at least one ECG signal.

18. A system for electrocardiogram (ECG) analysis, the system comprising non-transitory computer readable media storing instructions that, when executed by at least one processor, cause at least one computer to:
display a global view on a main plot of a graphic representation of at least one ECG signal in a first time window;
visually highlight, on the main plot, a plurality of episodes and/or events identified by analyzing the at least one ECG signal;
display a local view of the graphic representation of the at least one ECG signal in a second time window, wherein the first time window comprises the second time window;
display an intermediate view of the graphic representation of the at least one ECG signal in a third time window, wherein the third time window comprises the second time window and has a duration between a duration of the first time window and a duration of the second time window;
display at least one episode plot of the graphic representation of the ECG signal corresponding to at least one episode and/or event of the plurality of episodes and/or events that is visually highlighted on the main plot, the at least one episode plot depicting the at least one episode and/or event;
select a timepoint on the main plot responsive to slidable interaction of a cursor on a time bar;
cause simultaneous adaptation of the graphic representation of the at least one ECG signal in the local view and the intermediate view based on sliding of the cursor to a selected timepoint on the time bar; and
cause, in response to selecting the at least one episode plot of the graphic representation of the ECG signal, the cursor to automatically move on the time plot to a timeframe at a beginning or an end of the at least one episode and/or event, or between the beginning and the end of the at least one episode and/or event.

19. The system of claim 18, wherein the instructions, when executed by the at least one processor, cause the at least one computer to:
delineate the at least one ECG signal; and
classify the at least one ECG signal that has been delineated to identify the plurality of episodes and/or events.

20. The system of claim 19, wherein the instructions, when executed by the at least one processor, cause the at least one computer to label, based on the classifying, ECG segments of the at least one ECG signal that are associated with an abnormality in the at least one ECG signal.

21. The computer-implemented method according to claim 1, wherein the at least one interactive interface is configured to select the timepoint on the main plot in response to the cursor sliding to an episode and/or event of the plurality of episodes and/or events identified during the analysis of the ECG signal using the time bar.

22. The interactive electrocardiogram analysis system according to claim 10, wherein the at least one interactive interface is configured to select the timepoint on the main plot in response to the cursor sliding to a highlighted episode and/or event of the plurality of episodes and/or events using the time bar.

23. The computer-implemented method of claim 15, wherein selecting the timepoint comprises selecting the timepoint on the main plot associated with a highlighted episode and/or event of the plurality of episodes and/or events responsive to slidable interaction of the cursor on the time bar.

24. The system of claim 18, wherein selecting the timepoint comprises selecting the timepoint on the main plot associated with a highlighted episode and/or event of the plurality of episodes and/or events responsive to slidable interaction of the cursor on the time bar.

* * * * *